United States Patent
Pameijer et al.

(10) Patent No.: US 10,602,960 B2
(45) Date of Patent: Mar. 31, 2020

(54) LOCATING DEVICE

(71) Applicant: Cook Medical Technologies LLC, Bloomington, IN (US)

(72) Inventors: Preston R Pameijer, Bloomington, IN (US); Michael R Kurrus, Ellettsville, IN (US); Anthony D Hammack, Bloomington, IN (US); Joseph D Schilling, Bloomington, IN (US); Andreas F Shick, Grand Blanc, MI (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 582 days.

(21) Appl. No.: 14/338,561

(22) Filed: Jul. 23, 2014

(65) Prior Publication Data

US 2015/0031987 A1    Jan. 29, 2015

Related U.S. Application Data

(60) Provisional application No. 61/857,736, filed on Jul. 24, 2013, provisional application No. 61/927,648, filed on Jan. 15, 2014.

(51) Int. Cl.
*A61B 5/05* (2006.01)
*A61B 5/06* (2006.01)
(Continued)

(52) U.S. Cl.
CPC ............ *A61B 5/065* (2013.01); *A61B 5/0084* (2013.01); *A61B 5/042* (2013.01);
(Continued)

(58) Field of Classification Search
CPC ...... A61M 25/0105; A61M 2025/0166; A61B 1/00; A61B 5/065; A61B 5/042;
(Continued)

(56) References Cited

U.S. PATENT DOCUMENTS 4,248,214 A  2/1981 Hannah et al.
4,444,185 A  4/1984 Shugar
(Continued)

OTHER PUBLICATIONS

Mauro Pittiruti, MD, "PICC Positioning Using the EXG Method to Verify Tip Location," AVA 2009, Sep. 15-17, Las Vegas, NV, pp. 1-23.
(Continued)

*Primary Examiner* — Joel F Brutus
(74) *Attorney, Agent, or Firm* — Brinks Gilson & Lione

(57) ABSTRACT

A device and method are described for navigating and positioning a central venous catheter into the venous system using two different modes of location. For example, a peripherally inserted central catheter ("PICC") may be navigated and positioned within the superior vena cava. A light emitting element is used in the first mode to navigate the PICC to the superior vena cava. To improve visibility during navigation, the light emitted from the light emitting element may include a narrow range of wavelengths that generally matches the wavelengths of light that are transmissable through a light absorbing material defining the wall of the catheter. A conductive medium is used in the second mode to monitor an ECG signal in order to position the PICC in the superior vena cava. One advantage of this procedure is that X-ray visualization can be eliminated to reduce the danger associated with X-rays.

18 Claims, 17 Drawing Sheets

(51) Int. Cl.
*A61B 5/00* (2006.01)
*A61B 5/042* (2006.01)
*A61M 25/01* (2006.01)
A61B 34/20 (2016.01)
A61B 90/30 (2016.01)

(52) U.S. Cl.
CPC ....... *A61M 25/0105* (2013.01); *A61B 5/6851* (2013.01); *A61B 5/6852* (2013.01); *A61B 2034/2051* (2016.02); *A61B 2034/2055* (2016.02); *A61B 2090/306* (2016.02); *A61M 2025/0166* (2013.01)

(58) Field of Classification Search
CPC .......... A61B 5/0084; A61B 2034/2051; A61B 2090/306; A61B 5/6852; A61B 5/6851
See application file for complete search history.

(56) References Cited

U.S. PATENT DOCUMENTS

| | | |
|---|---|---|
| 4,566,438 A | 1/1986 | Liese et al. |
| 4,567,882 A | 2/1986 | Heller |
| 4,607,622 A | 8/1986 | Fritch et al. |
| 4,684,245 A | 8/1987 | Goldring |
| RE32,718 E | 7/1988 | Andersson et al. |
| 4,898,175 A | 2/1990 | Noguchi |
| 4,905,698 A | 3/1990 | Strohl, Jr. et al. |
| 4,921,326 A | 5/1990 | Wild et al. |
| RE33,234 E | 6/1990 | Landry |
| 5,131,380 A | 7/1992 | Heller et al. |
| 5,370,640 A | 12/1994 | Kolff |
| 5,423,321 A | 6/1995 | Fontenot |
| 5,445,142 A | 8/1995 | Hassler |
| 5,580,147 A | 12/1996 | Salerno |
| 5,662,585 A | 9/1997 | Willis et al. |
| 5,728,092 A | 3/1998 | Doiron et al. |
| 5,891,133 A * | 4/1999 | Murphy-Chutorian ............... A61B 18/24 606/15 |
| 5,902,247 A | 5/1999 | Coe et al. |
| 5,954,652 A | 9/1999 | Heyman |
| 5,993,382 A | 11/1999 | Pruitt, Sr. |
| 6,129,662 A | 10/2000 | Li et al. |
| 6,176,824 B1 | 1/2001 | Davis |
| 6,230,046 B1 | 5/2001 | Crane et al. |
| 6,246,901 B1 | 6/2001 | Benaron |
| 6,308,092 B1 | 10/2001 | Hoyns |
| 6,366,726 B1 | 4/2002 | Wach et al. |
| 6,387,043 B1 | 5/2002 | Yoon |
| 6,398,755 B1 * | 6/2002 | Belef ...................... A61B 8/12 604/95.01 |
| 6,436,116 B1 | 8/2002 | Spitz et al. |
| 6,994,667 B2 | 2/2006 | Singh |
| 7,062,306 B2 | 6/2006 | Benaron et al. |
| 7,252,677 B2 | 8/2007 | Burwell et al. |
| 7,273,056 B2 | 9/2007 | Wilson et al. |
| 7,329,223 B1 | 2/2008 | Ainsworth et al. |
| 7,366,563 B2 | 4/2008 | Kleen et al. |
| 7,470,230 B2 | 12/2008 | Smith et al. |
| 7,559,892 B2 | 7/2009 | Adler et al. |
| 7,559,925 B2 | 7/2009 | Goldfarb et al. |
| 7,757,695 B2 | 7/2010 | Wilson et al. |
| 7,783,338 B2 | 8/2010 | Ainsworth et al. |
| 7,811,225 B2 | 10/2010 | Sauer et al. |
| 7,905,698 B2 | 3/2011 | Liu et al. |
| 7,917,193 B2 | 3/2011 | Crane |
| 7,952,719 B2 | 5/2011 | Brennan, III |
| 7,992,573 B2 | 8/2011 | Wilson et al. |
| 8,070,767 B2 | 12/2011 | Smith |
| 8,078,261 B2 | 12/2011 | Imam |
| 8,142,422 B2 | 3/2012 | Makower et al. |
| 8,346,346 B1 | 1/2013 | Schnitzer et al. |
| 8,437,833 B2 | 5/2013 | Silverstein |
| 8,498,694 B2 | 7/2013 | McGuire, Jr. et al. |
| 8,500,730 B2 | 8/2013 | Lee et al. |
| 8,548,572 B2 | 10/2013 | Crane |
| 2001/0007070 A1 * | 7/2001 | Stewart ............... A61B 18/1492 606/41 |
| 2005/0004554 A1 | 1/2005 | Osborne |
| 2006/0217793 A1 * | 9/2006 | Costello ................. A61N 1/056 607/122 |
| 2007/0073160 A1 * | 3/2007 | Imam .................. A61B 5/15003 600/476 |
| 2007/0225695 A1 | 9/2007 | Mayer et al. |
| 2007/0244371 A1 | 10/2007 | Nguyen et al. |
| 2008/0015413 A1 | 1/2008 | Barlow et al. |
| 2008/0039715 A1 * | 2/2008 | Wilson ..................... A61B 5/06 600/424 |
| 2008/0194973 A1 | 8/2008 | Imam |
| 2008/0228066 A1 | 9/2008 | Waitzman |
| 2008/0228085 A1 | 9/2008 | Jenkins et al. |
| 2008/0243002 A1 * | 10/2008 | Munce ................. A61B 5/0062 600/459 |
| 2009/0005675 A1 * | 1/2009 | Grunwald .............. A61B 5/042 600/424 |
| 2009/0156826 A1 | 6/2009 | Papamichelakis et al. |
| 2009/0156926 A1 | 6/2009 | Messerly et al. |
| 2009/0177090 A1 | 7/2009 | Grunwald et al. |
| 2009/0240248 A1 * | 9/2009 | Deford ............... A61B 18/1492 606/41 |
| 2009/0318912 A1 | 12/2009 | Mayer et al. |
| 2010/0016664 A1 | 1/2010 | Viola |
| 2010/0016844 A1 * | 1/2010 | Patel, Jr. .............. A61B 5/0084 606/15 |
| 2010/0262069 A1 * | 10/2010 | Rabiner ............. A61B 17/7097 604/21 |
| 2010/0280328 A1 | 11/2010 | Nguyen et al. |
| 2010/0317981 A1 | 12/2010 | Grunwald et al. |
| 2010/0318026 A1 * | 12/2010 | Grunwald .......... A61B 5/04017 604/95.05 |
| 2011/0015533 A1 * | 1/2011 | Cox ....................... A61B 5/042 600/509 |
| 2011/0166442 A1 | 7/2011 | Sarvazyan |
| 2011/0270080 A1 | 11/2011 | Crane |
| 2012/0083689 A1 | 4/2012 | Imam |
| 2012/0136242 A1 * | 5/2012 | Qi ........................... A61B 5/026 600/424 |
| 2012/0184924 A1 | 7/2012 | Ejike et al. |
| 2012/0190973 A1 | 7/2012 | Ressemann et al. |
| 2012/0253186 A1 * | 10/2012 | Simpson ........ A61B 17/320758 600/426 |
| 2012/0316433 A1 | 12/2012 | Maruyama |
| 2013/0018248 A1 * | 1/2013 | Hurezan .................. A61B 5/06 600/381 |
| 2013/0046137 A1 | 2/2013 | Zhao et al. |
| 2013/0046172 A1 | 2/2013 | Waitzman et al. |
| 2013/0072943 A1 | 3/2013 | Parmar |
| 2013/0231533 A1 * | 9/2013 | Papademetriou .. A61B 1/00043 600/110 |
| 2013/0310823 A1 * | 11/2013 | Gelfand ............. A61B 18/1492 606/33 |

OTHER PUBLICATIONS

Gebhard et al., "The Accuracy of Electrocardiogram-Controlled Central Line Placement," International Anesthesia Research Society, vol. 104, No. 1, Jan. 2007, pp. 1-6.

Mauro Pittiruti et al., "The Electrocardiographic Method for Positioning the Tip of Central Venous Catheters," JVase Access Oct.-Dec. 12, 2011 (4); 280-91, pp. 1-12.

* cited by examiner

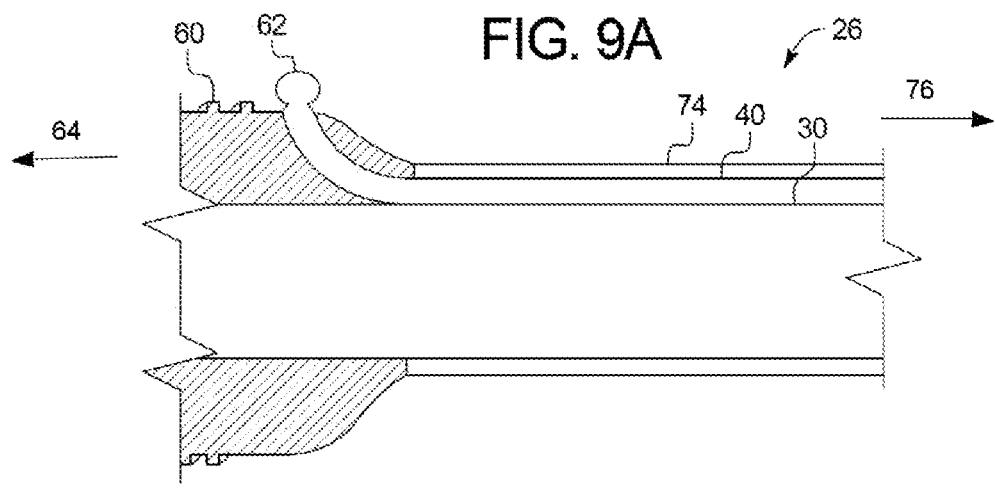
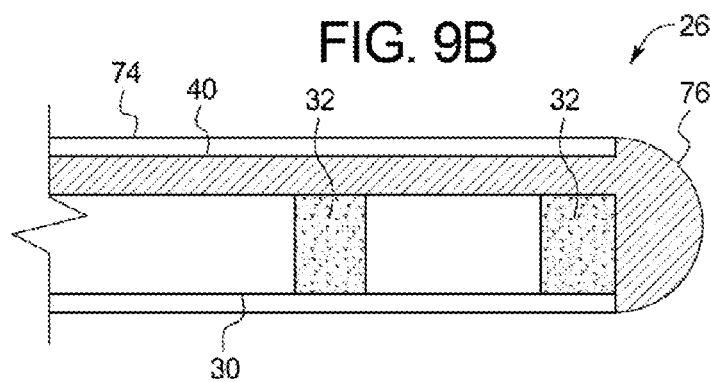
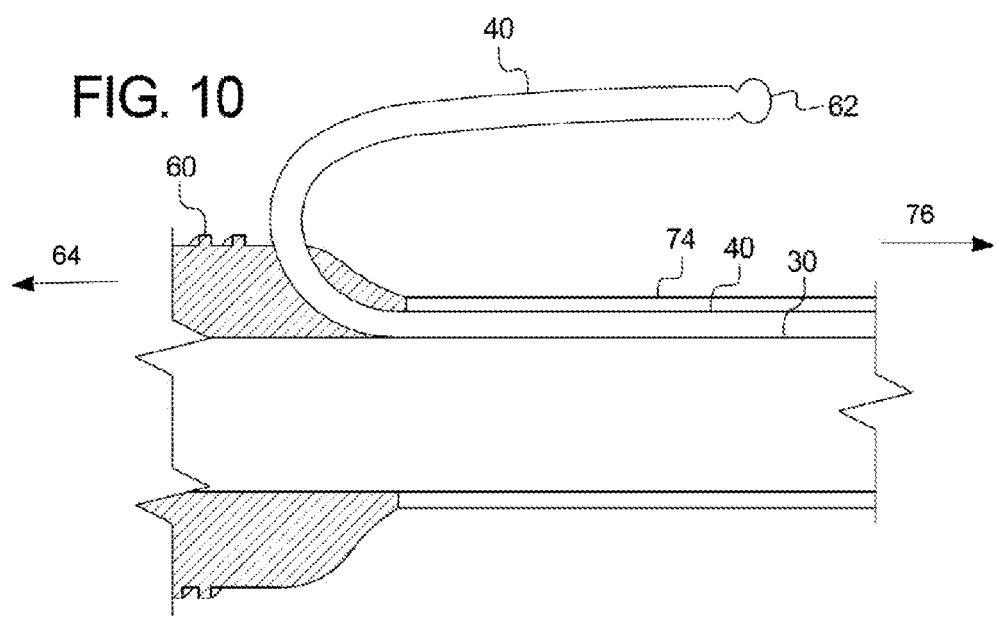

A-A

LOCATING DEVICE

This application claims priority to U.S. Provisional Application No. 61/927,648, filed Jan. 15, 2014, and U.S. Provisional Application No. 61/857,736, filed Jul. 24, 2013, both of which are hereby incorporated by reference herein.

BACKGROUND

The present invention relates generally to medical devices and more particularly to a device and method for navigating a catheter through a body passageway. In one preferred embodiment, the invention involves navigating a peripherally inserted central catheter to the superior vena cava and positioning the peripherally inserted central catheter within the superior vena cava or right atrium for treatment. In another preferred embodiment, the invention involves transmitting light through the tubular wall of a catheter and overlying body tissues for external navigation, where the tubular wall of the catheter is made of a material that absorbs certain wavelengths of light and the light source emits light within a limited wavelength range that is transmissable through the light absorbing material.

One type of central venous catheter is referred to as peripherally inserted central catheters ("PICC"), which are commonly used for infusing drugs or nutrition into a patient's body and for venous pressure monitoring, blood sampling, administration of fluids, and for the delivery of contrast solution for imaging studies. As those of ordinary skill in the art understand the distal portion of a PICC is typically positioned within the superior vena cava of a patient. Although various locations may be prescribed for the distal end of the PICC, one common position where the distal end of the PICC may be located is the lower one third of the superior vena cava. The use of PICCs in the superior vena cava is desirable for a number of treatments since the entire blood flow through a patient's body passes through the superior vena cava to the heart, and is then recirculated through the patient's body. As a result, drugs and nutrition infused into the superior vena cava are quickly diluted and evenly distributed throughout the patient's body.

For example, chemotherapy drugs, and other such drugs, are often released into the body through a PICC to the superior vena cava. The superior vena cava is particularly advantageous for the release of chemotherapy drugs because chemotherapy drugs can be harmful to the tissues of the vessel walls. However, because of the high flow rate of blood in the superior vena cava, chemotherapy drugs are less likely to harm the tissues of the superior vena cava, and the chemotherapy drugs are quickly and evenly distributed throughout the patient's body. The use of PICCs in the superior vena cava are also commonly used for the infusion of total parenteral nutrition to patients, pressure monitoring of the venous system, and imaging or contrast studies. Depending on the particular treatment being performed, a PICC may remain within the superior vena cava anywhere from less than an hour to more than a year.

One difficulty with the use of PICCs is that the PICC must be navigated and positioned through the venous system to the superior vena cava from outside the patient's body. Thus, the physician has limited means for observing the location of the PICC as it is being navigated and positioned. The most common methods of observing the PICC involve the use of X-rays to view navigation in process or to confirm final positioning. For example, fluoroscopy uses X-rays to provide a video image which can be used to view movement of the PICC or guidewire as it is navigated through the venous system. Alternatively, the PICC may be navigated through the venous system without the use of external visualization by relying on anatomical measurements, tactile feedback during navigation, and physician experience. However, even in this blind type of navigation, an X-ray image is usually taken after navigation is complete to confirm final positioning of the PICC before using the PICC for therapy.

An approach for navigating and positioning a PICC that does not involve the use of X-rays would be desirable since X-ray radiation is dangerous for patients and physicians. One alternative that has been tried is the use of an optical fiber within the PICC that shines light that can be seen through thinner tissues from outside of a patient's body. However, the use of an optical fiber has limited usefulness because final positioning of a PICC occurs within the superior vena cava underneath the sternum where the light from an optical fiber cannot be seen from outside of the patient, both due to the sternum bone blocking the light and the depth of superior vena cava and overlying tissues. Another alternative that has been tried is the use of intravascular ECG to position a PICC within the superior vena cava. However, this technique can only be used for final positioning and cannot be used to navigate a PICC into the superior vena cava, since the readings needed to determine positioning only become noticeably apparent proximate the heart. Thus, in this approach blind navigation has been used to thread the PICC through the venous system to the superior vena cava.

Accordingly, the inventors believe it would be desirable to provide a simple and inexpensive way to navigate and position a catheter without using X-rays.

SUMMARY

A device and method is described that may be used to navigate and position a PICC into a superior vena cava using two modes that do not require X-ray visualization. The first mode uses a light emitting element to enable light navigation to the superior vena cava. The second mode uses a conductive medium to monitor an intravascular ECG reading to position the PICC within the superior vena cava or right atrium. Combining these two modes into a single device and/or method enables the entire insertion procedure to be performed from the access site to the final position in the superior vena cava without using X-ray visualization.

A system for navigating is also provided with a locating device having a light emitting element positioned within the lumen of a catheter. The light emitting element directs light toward the catheter wall, and the catheter wall includes a light absorbing material. The light absorbing material is defined by first and second wavelengths of light, where a higher proportion of light passes through the first range than the second range. A light source is provided that emits wavelengths of light that generally matches the first range of wavelengths.

The inventions herein may also include any other aspect identified below, described in the written description, the claims, or in the attached drawings and any combination thereof.

A system for locating a central venous catheter, comprising:

a central venous catheter comprising one or more lumens extending therethrough adapted to extend from a proximal portion outside an access site into a patient's vein to a distal end within a venous system of the patient;

a locating device extending through one of the lumens of the central venous catheter, a proximal portion of the locating device extending proximally from the proximal portion of the central venous catheter, and a distal portion of the locating device being disposed adjacent the distal end of the central venous catheter, the locating device being removable from the central venous catheter after the central venous catheter is navigated and positioned within the venous system;

a biocompatible fluid disposed within the lumens of the central venous catheter;

a light emitting element disposed along the distal portion of the locating device, the light emitting element thereby being adapted to direct light radially away from the locating device, the light being visible through tissues of the patient from outside the patient to navigate the central venous catheter through the venous system; and a conductive member made of a metallic material electrically connected to an ECG machine, a distal portion of the conductive member being exposed to the biocompatible fluid within one of the lumens of the central venous catheter or blood within the patient adjacent the distal end of the central venous catheter, the conductive member thereby being adapted to transmit an intravascular ECG signal to the ECG machine to position the central venous catheter within the venous system.

The system where the locating device comprises an optical fiber adapted to extend from the proximal portion of the locating device to the distal portion of the locating device, the light emitting element comprising a redirection element disposed along the optical fiber, the redirection element being adapted to direct light passing axially through the optical fiber radially away from the optical fiber, and a light source connected to a proximal end of the optical fiber.

The system where the redirection element comprises a partially or completely removed length of a cladding layer of the optical fiber.

The system where a distal end of the optical fiber is adjacent the distal end of the central venous catheter.

The system further comprising an adapter connected to the light source and a proximal hub connected to the optical fiber, the proximal hub and the adapter being adapted to couple the light source and the optical fiber together for the transmission of light from the light source to the optical fiber, the proximal hub comprising a flexible arm engaging a tapered portion of the adapter, where pressure from the flexible arm against the tapered portion pulls the proximal hub into the adapter until a proximal end of the optical fiber is generally flush with a lens of the light source.

The system where the locating device comprises an electric supply line adapted to extend from the proximal portion of the locating device to the distal portion of the locating device, the light emitting element comprising a light source connected to a distal end of the electric supply line and adapted to direct light radially away from the locating device, and a power supply connected to a proximal end of the electric supply line.

The system where the conductive member wraps around an outer circumference of a length of the proximal portion of the locating device, the conductive member thereby being exposed proximally from the proximal portion of the central venous catheter, and the conductive member being connectable to the ECG machine with a clip contacting the outer circumference.

The system where the conductive member comprises a coiled wire wrapped around the outer circumference of the length.

The system where the conductive member extends axially through one of the lumens of the central venous catheter less than half of an overall length of the central venous catheter.

The system where the conductive member extends axially through one of the lumens of the central venous catheter substantially an entire length of the central venous catheter.

The system where the locating device extends through a valve to extend through the lumen of the central venous catheter, the valve longitudinally retaining the central venous catheter and the locating device together during navigation and positioning of the central venous catheter.

The system further comprising a proximal member housing a light source or a power supply, a sterile barrier surrounding the proximal member, and a proximal end of the locating device comprises a conical surface configured to penetrate the sterile barrier to connect the locating device to the proximal member.

The system further comprising an ECG extension cable comprising a clip at one end adapted to connect to the conductive member and an ECG electrode snap at another end adapted to connect to an ECG lead.

The system further comprising an ECG electrode snap fixedly attached to the conductive member along a proximal portion of the conductive member.

The system where the ECG electrode snap is disposed more than 300 mm from the access site when the distal portion of the conductive member is within the venous system.

The system further comprising a proximal member housing a light source or a power supply connected to a proximal end of the locating device, the proximal member being disposed more than 150 mm from the access site when the distal portion of the locating device is within the venous system.

The system where the locating device and the conductive member are bonded together to restrain longitudinal movement between the locating device and the conductive member.

The system where the locating device is disposed coaxially within the conductive member.

The system where the locating device comprises an optical fiber adapted to extend from the proximal portion of the locating device to the distal portion of the locating device, the light emitting element comprising a redirection element disposed along the optical fiber, the redirection element being adapted to direct light passing axially through the optical fiber radially away from the optical fiber, and a light source connected to a proximal end of the optical fiber, the conductive member wraps around an outer circumference of a length of the proximal portion of the locating device, the conductive member thereby being exposed proximally from the proximal portion of the central venous catheter, and the conductive member being connectable to the ECG machine with a clip contacting the outer circumference, the locating device is disposed coaxially within the conductive member, the locating device and the conductive member are bonded together to restrain longitudinal movement between the locating device and the conductive member, and the locating device and the conductive member extend through a valve to extend through the lumen of the central venous catheter, the valve longitudinally retaining the central venous catheter and the locating device and the conductive member together during navigation and positioning of the central venous catheter.

The system where a distal end of the optical fiber is adjacent the distal end of the central venous catheter, the redirection element comprises a partially or completely removed length of a cladding layer of the optical fiber, the conductive member comprises a coiled wire wrapped around the outer circumference of the length, and the conductive member extends axially through the lumen of the central venous catheter less than half of an overall length of the central venous catheter.

A method of locating a central venous catheter within a venous system of a patient, comprising:

extending a locating device and a conductive medium though one or more lumens of the central venous catheter, the locating device comprising a light emitting element disposed adjacent a distal end thereof;

establishing access to a vein within an arm or neck of the patient;

directing light from the light emitting element radially away from the locating device;

navigating the central venous catheter through a venous system of the patient by viewing the light from outside of the patient; and positioning a distal portion of the central venous catheter within the venous system by monitoring an ECG reading through the conductive medium.

A system for navigating a catheter through a body passageway of a patient, comprising:

a catheter comprising a distal portion and a proximal portion, the distal portion comprising a tubular wall defining a lumen extending therethrough, the tubular wall being at least partially translucent and defined by a first range of visible light wavelengths and a second range of visible light wavelengths, the first range of visible light wavelengths comprising less than 50% of the entire visible light spectrum and the second range of visible light wavelengths comprising more than 50% of the entire visible light spectrum, the first range being at least partially transmitted through the tubular wall and the tubular wall substantially blocks transmission of all visible light wavelengths within the second range, where the first range appears as a color of red, orange, yellow, green, blue, violet or a mixture thereof when a white light is transmitted through the tubular wall;

a locating device extending through the lumen of the catheter, the locating device comprising a light emitting element disposed along a distal portion thereof, the light emitting element being disposed within the lumen and being directed toward the tubular wall; and a light source in communication with the light emitting element, at least 60% of light output by the light source being within the first range of visible light wavelengths and no more than 30% of the light output being within the second range of visible light wavelengths, where the light output is directed through the tubular wall by the light emitting element, the light output being visible from an exterior of the patient through the tubular wall and overlying tissues of the patient for navigation through the body passageway.

The system where the tubular wall comprises a structural base material and an additive, the structural base material being defined by generally uniform light transmission therethrough throughout the entire visible light spectrum, and the additive having greater light absorbing properties throughout the second range and transmitting light throughout the first range.

The system where the additive is impregnated within the tubular wall of the catheter and is exposed to an exterior surface and an interior surface of the tubular wall.

The system where the additive is a drug.

The system where the drug comprises an antibiotic drug.

The system where the drug comprises minocycline and rifampin.

The system where the catheter is a central venous catheter.

The system where the light emitting element is within 50 mm of a distal tip of the catheter.

The system where the light source is an LED.

The system where substantially all of the light output by the light source is within the first range of visible light wavelengths.

The system where substantially none of the light output by the light source is within the second range of visible light wavelengths.

The system where the light output of the light source comprises a single peak.

The system where a white light transmitted through the tubular wall appears as a color of one of red, orange, yellow, green, blue or violet.

The system where the second range comprises more than 75% of the entire visible light spectrum.

The system where the first range of visible light wavelengths is within 580 nm and 750 nm.

The system where at least 60% of the light output of the light source is within 600 nm and 700 nm.

The system where the tubular wall is orange or red.

The system where the light output is orange or red.

The system where the tubular wall comprises a structural base material and an additive, the structural base material being defined by generally uniform light transmission therethrough throughout the entire visible light spectrum, and the additive having greater light absorbing properties throughout the second range and transmitting light throughout the first range, the additive is a drug, the first range of visible light wavelengths is within 580 nm and 750 nm, and the light output of the light source comprises a single peak.

The system where the light emitting element is within 50 mm of a distal tip of the catheter, and substantially none of the light output by the light source is within the second range of visible light wavelengths.

BRIEF DESCRIPTION OF SEVERAL VIEWS OF THE DRAWINGS

The invention may be more fully understood by reading the following description in conjunction with the drawings, in which:

FIG. 9A is a cross-sectional view of the proximal portion of another locating device;

FIG. 9B is a cross-sectional view of the distal portion of the locating device;

FIG. 10 is a cross-sectional view of the proximal portion of another embodiment of the locating device;

DETAILED DESCRIPTION

Figure 1:
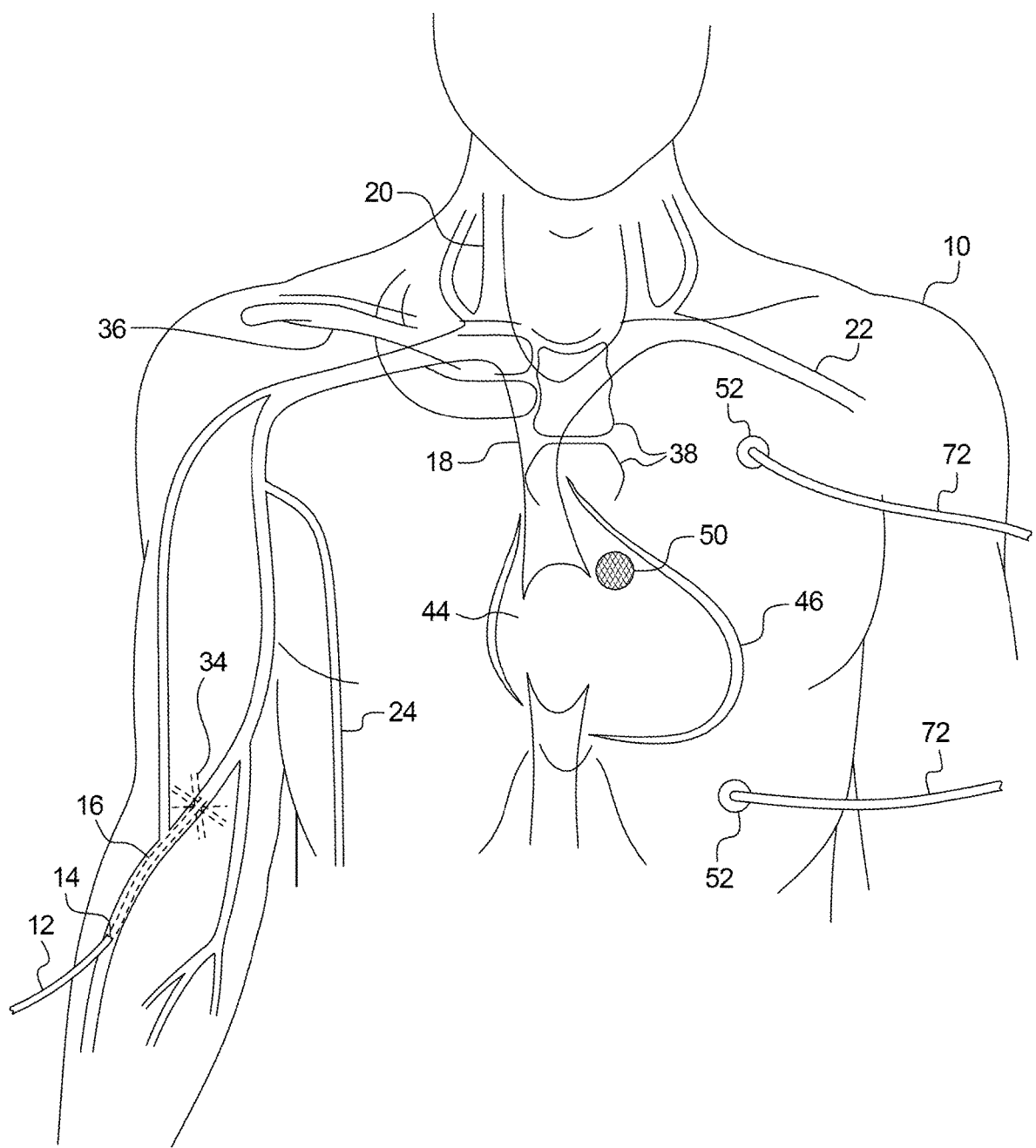
FIG. 1 is a schematic view of a patient's venous system.

Referring now to the figures, and particularly to FIG. 1, the internal anatomy of a patient is shown. As those of ordinary skill in the art understand, a peripherally inserted central catheter ("PICC") 12 is typically inserted through an access site 14 into one of the veins 16 of the arm, such as the cephalic vein 16, basilic vein or brachial vein. The PICC 12 is then navigated through the venous system until the distal portion of the PICC 12 is positioned within the superior vena cava 18. When the distal portion of the PICC 12 reaches the superior vena cava 18, the physician will typically position the distal portion at a predetermined location as desired by the physician for the particular treatment involved. For example, for many treatments it is desirable for the distal opening of the PICC 12 to be located within the lower ⅓ of the superior vena cava 18. However, it is also possible that a physician may desire to locate the distal opening of the PICC 12 within the right atrium of the heart.

Navigating a PICC 12 through a patient's venous system to reach the superior vena cava 18 can be challenging, and it is not unusual for a PICC 12 to be inadvertently navigated through the wrong veins so that the distal portion of the PICC 12 misses the superior vena cava 18. The most common malpositions are for the PICC 12 to be navigated up through the jugular vein 20, to be navigated across through the transverse brachiocephalic and opposite subclavian vein 22, or to be navigated down through the thoracic vein 24 on the side of the torso where access is gained. As explained above, physicians most commonly avoid these malpositions when navigating a PICC 12 through the venous system by using fluoroscopy during the navigation process, or alternatively physicians discover a malposition before treatment begins by taking an X-ray image. Fluoroscopy or an X-ray image is also commonly used to precisely position the PICC 12 within the superior vena cava 18 after the PICC 12 is navigated through the venous system. Typically, the overall length of the PICC 12 is trimmed prior to the procedure for the particular anatomy of the patient 10, and some extra length is left on the PICC 12 so that the proximal portion can be adjusted at the access site 14 in order to precisely position the distal portion in the superior vena cava 18.

The invention described herein has the advantage of making it possible to both navigate a PICC 12 through the venous system while avoiding malpositions and positioning the distal portion of the PICC 12 in the superior vena cava 18 without using X-rays. Thus, the entire procedure of inserting a PICC 12 may be done without using dangerous X-rays. The invention accomplishes this by using two different navigation and positioning techniques in a single device and/or method. In particular, the invention uses a light emitting element 32, 116 for navigation through the venous system and uses intravascular ECG via an internal conductor 40, 80 and an ECG machine for positioning the PICC 12 in the superior vena cava 18.

As described further below, the locating device 26, 78, 96, 114 preferably extends through a lumen of a PICC 12 and has a distal end that is adjacent the distal end of the PICC 12. A valve 28 (FIGS. 3 and 12-14), such as a tuohy-borst valve 28, may be connected to the proximal end of the PICC 12 and may seal around the circumference of the locating device 26, 78, 96, 114, both to prevent blood from escaping from the PICC 12 and to longitudinally retain the PICC 12 and locating device 26, 78, 96, 114 together during the navigating and positioning procedure. The distal portion of the optical fiber 30 is provided with a redirection element 32, or light emitting element 32, that directs light that passes axially through the optical fiber 30 radially away from the optical fiber 30. Alternatively, the light emitting element 32 may be an LED 116 along the distal portion supplied with electric power by electric supply lines 118 as in FIG. 21. As illustrated in FIG. 1, the light 34 directed radially away from the locating device 26, 78, 96, 114 is bright enough that it shines 34 through the tissues between the venous system and the patient's skin and is visible to the naked eye from outside of the patient 10. Thus, the physician may view the light 34 from the light emitting element 32 to see the location of the PICC 12 and the locating device 26, 78, 96, 114 within the venous system. As a result, the physician may navigate the PICC 12 through the venous system by viewing the light 34 from the light emitting element 32 without using fluoroscopy. Although various wavelengths of light may be used for the light navigation described herein, particular wavelengths may be more preferred. For example, light with a long wavelength within the visible light spectrum, such as orange and red light, may be better at penetrating through tissues, and may therefore be more visible. It may also be particularly useful to match the color of the light with the color of the PICC 12. That is, the wavelengths of light emitted by the light source 64, 116 may be primarily within a narrow range of wavelengths of light that are not absorbed by the PICC 12. For example, where the color of the PICC 12 is orange, it may be desirable for the light to also be within the orange spectrum. Specifically, a wavelength of 580 to 635 nm or 590 to 610 nm may be desirable for the light. Alternatively, white light with a mixture of various wavelengths may also be used.

Navigating the PICC 12 through the venous system by viewing light 34 from the light emitting element 32 will typically work while the distal portion of the PICC 12 and the locating device 26, 78, 96, 114 are within veins that are close to the surface of the skin and not behind larger bones. However, the light from the light emitting element 32 typically becomes obstructed and cannot be sufficiently seen when thicker tissues exist between a vein and the surface of the skin and where bones are located between the vein and skin. When using the locating device 26, 78, 96, 114 to navigate a PICC 12 through the venous system, the light 34 from the light emitting element 32 will typically be viewable from the access site 14 up to the clavicle bone 36 but will be obstructed for a short distance as the light emitting element 32 passes under the clavicle 36. The light 34 may then be briefly viewable again between the clavicle bone 36 and the sternum bone 38. Brief obstruction of the light 34 at the clavicle 36 may be overcome by providing multiple light emitting elements 32 along the length of the locating device 26, 78, 96, 114 so that at least one of the light emitting elements 32 is viewable as the locating device 26, 78, 96, 114 passes under the clavicle 36. However, because the superior vena cava 18 is located underneath the sternum bone 38, the light 34 from the light emitting element 32 will no longer be viewable in most cases as the locating device 26, 78, 96, 114 and PICC 12 enter the superior vena cava 18. Thus, the light emitting element 32 is unusable for positioning the distal portion of the PICC 12 within the superior vena cava 18. Nevertheless, the light emitting element 32 is useful for navigating the PICC 12 into the superior vena cava 18 since the most common malpositions will be viewable by seeing the light 34 from the light emitting element 32 in those locations. That is, if the PICC 12 and locating device 26, 78, 96, 114 are inadvertently navigated into the jugular vein 20, opposite subclavian, jugular or brachiocephalic veins 22, or thoracic vein 24, there are no bones in those locations to obstruct the light 34 and the tissues are thin enough to allow the light 34 to reach the surface of the patient 10. Therefore, if the PICC 12 has been malpositioned during navigation and is not in the superior vena cava 18, the physician will be able to see that the PICC 12 is in the wrong position.

Figure 2A:
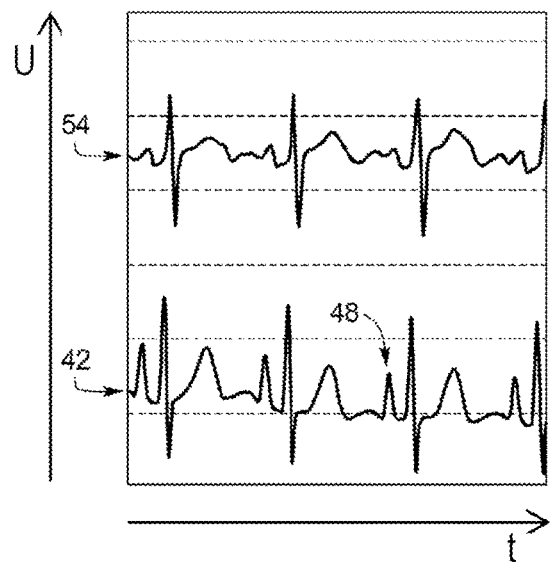
FIGS. 2A-2D are intravascular and external ECG readings, showing changes in the intravascular ECG readings as a conductive medium is moved toward the sinoatrial node.
Figure 2B:
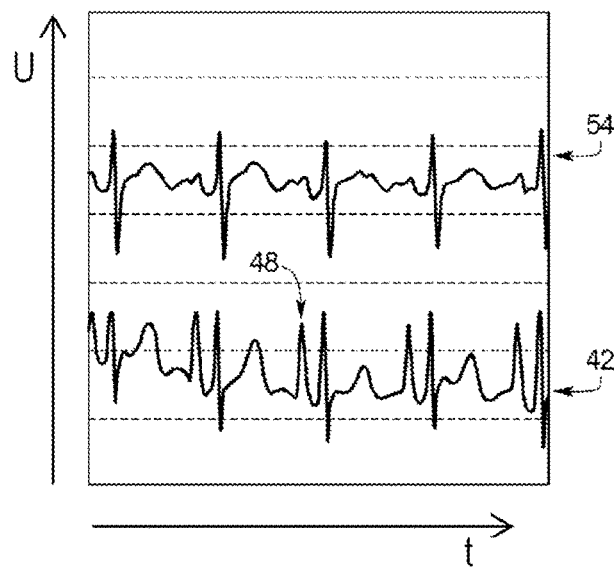
Figure 2C:
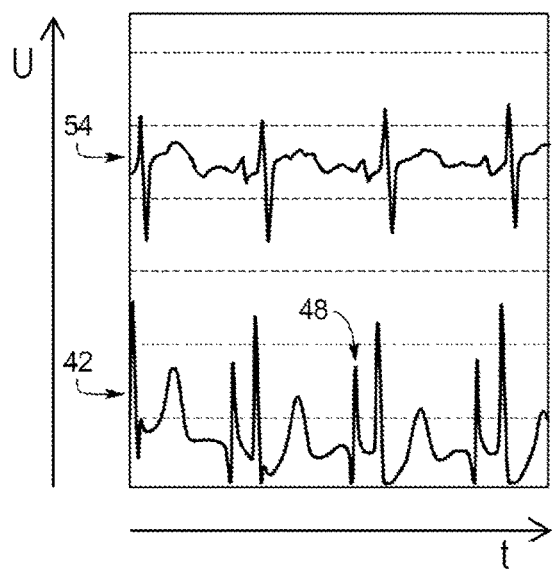
Figure 2D:
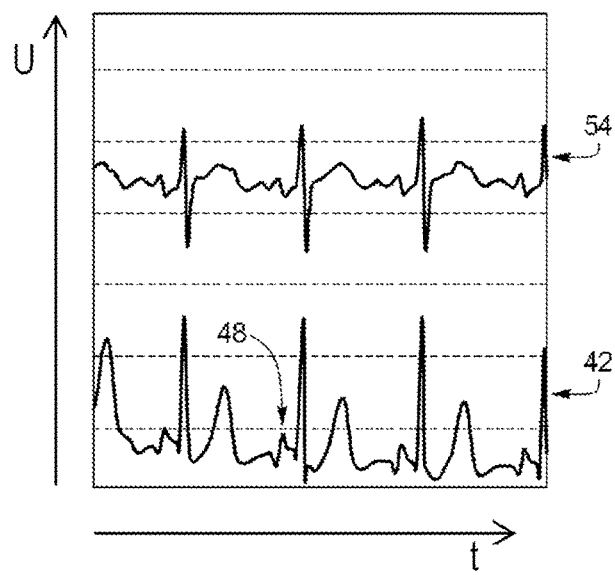

As noted, once the light emitting element 32 and PICC 12 are located within the superior vena cava 18, the outwardly directed light 34 will no longer be viewable from outside of the patient 10. However, in order to precisely position the PICC 12 in the superior vena cava 18, the locating device 26, 78, 96, 114 and method provides a second mode of determining the location of the PICC 12. The second mode of location is intravascular ECG, which requires a conductive medium 40, 80 that extends through the venous system from an ECG connector 62 for an ECG machine located outside of the patient 10 to a location within the superior vena cava 18. Intravascular ECG works by monitoring changes in the ECG signal 42 (e.g., lead II in Einthoven's triangle) as the conductive medium 40, 80 is moved through the superior vena cava 18 toward the right atrium 44 of the heart 46. In particular, as shown in FIGS. 2A-2D, the P-wave 48 of the ECG signal 42 changes as the conductive medium 40, 80 is moved closer to the sinoatrial ("SA") node 50 of the heart 46. Typically, as illustrated in FIG. 1, external ECG electrodes 52 will be applied to the skin of the patient's torso in order to compare the differences between the external electrode signals 54 and the signal 42 from the electrode 40, 80 within the superior vena cava 18. FIG. 2A illustrates an example of the end of the conductive medium 40, 80 located in the lower portion of the superior vena cava 18, where the P-wave 48 increases in height. By way of comparison, the external ECG reading 54 is shown along the top of each of FIGS. 2A-2D, while the intravascular ECG reading 42 is shown along the bottom of each figure. In FIG. 2B, the end of the conductive medium 40, 80 is located at the junction between the superior vena cava 18 and the right atrium 44 of the heart 46 (i.e., the cavoatrial junction), where the P-wave 48 is at its maximum height. In FIG. 2C, the end of the conductive medium 40, 80 is located in the upper portion of the right atrium 44 of the heart 46, where the P-wave 48 has a negative incision. And in FIG. 2D, the end of the conductive medium 40, 80 is located in the middle portion of the right atrium 44 of the heart 46, where the P-wave 48 has a diphasic pattern. As the conductive medium 40, 80 is moved further into the lower portion of the right atrium 44, the P-wave 48 will typically become completely negative. Thus, the distal portion of the PICC 12 may be accurately positioned within the superior vena cava 18 by monitoring the ECG reading 42 received through the conductive medium 40, 80.

Although intravascular ECG is useful for final positioning of the PICC 12 within the superior vena cava 18, this mode of location has little usefulness in navigating a PICC 12 from the access site 14 to the superior vena cava 18 since the changes in ECG readings 42 only become noticeably apparent when the conductive medium 40, 80 is relatively close to the SA node 50. For example, the ECG signal 42 may start to change about 10-15 cm from the SA node 50, and changes become more noticeable within about 5 cm from the SA node 50. However, because the invention combines light navigation and ECG positioning into a single device and method, a PICC 12 can be completely inserted from the access site 14 to the final position in the superior vena cava 18 without using X-rays. In addition, the ECG mode of positioning may also be useful in preventing a more rare type of malposition into the azygous vein. Although the light mode of navigating may not identify this malposition due to its deep location below the sternum 38, movement into the azygous typically would occur during the ECG positioning stage of the process, and changes in the ECG signal 42 may indicate that the locating device 26, 78, 96, 114 has unexpectedly moved away from the superior vena cava 18. Although this is a rare malposition, it is potentially a concern because a frontal X-ray image may not identify the malposition since the azygous vein extends rearward from the superior vena cava 18. Typically, a lateral X-ray image is required to identify a malposition within the azygous vein, which is more expensive and involves more exposure to X-rays.

Figure 3:
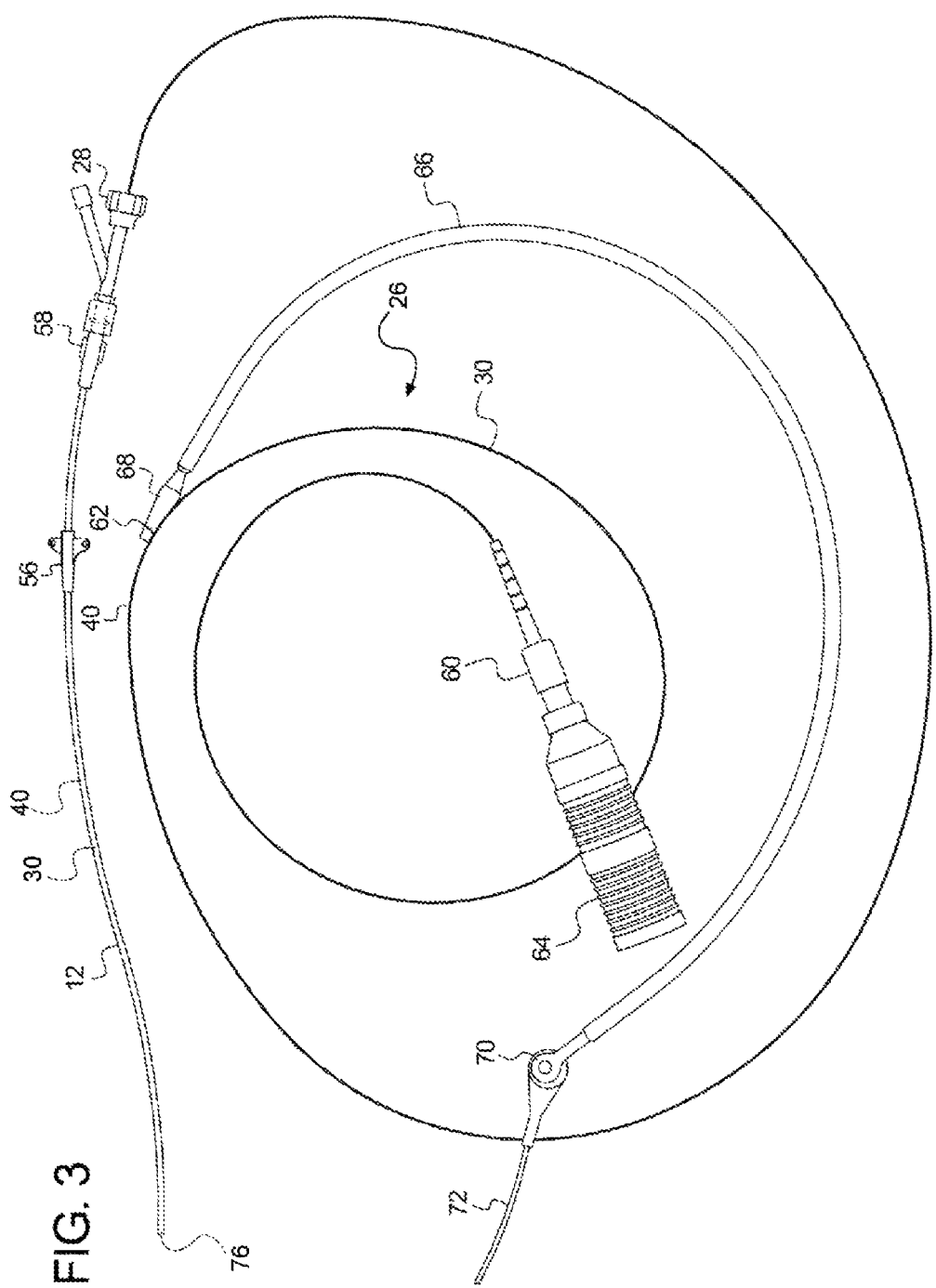
FIG. 3 is an elevational view of a peripherally inserted central catheter and a locating device.

One embodiment of the inventive device is shown in FIG. 3. As shown, the locating device 26 may extend through one or more of the lumens of the PICC 12. Preferably, the distal portion of the locating device 26 is positioned adjacent the distal end of the PICC 12 so that the distal ends are generally aligned. Typically, the distal portion of the locating device 26 is considered to be adjacent and generally aligned with the distal end of the PICC 12 when the variation in alignment is within a centimeter (i.e., the locating device 26 extends beyond the PICC 12 by a centimeter or the PICC 12 extends beyond the locating device 26 by a centimeter). The PICC 12 may have a first hub 56 that is sutured or otherwise attached to the patient's body 10 after the PICC 12 has been finally positioned to retain the position of the PICC 12. The PICC 12 may also have a second hub 58 which may have a luer fitting for attaching syringes or other devices to infuse drugs or nutrition through the PICC 12 during treatment. Various types of valves 28, such as the tuohy-borst valve 28 shown in FIGS. 3 and 12-14, may also be provided to seal the locating device 26 within the PICC 12 and lock the PICC 12 and locating device 26 together. The proximal portion of the locating device 26 extends proximally from the proximal end of the PICC 12 so that the physician can access the proximal portion of the locating device 26 while it is positioned within the PICC 12.

The locating device 26 has two separate connectors 60, 62 for connecting a light source 64, or proximal member 64, and an ECG machine to the locating device 26. In particular, a light source connector 60 may be provided along the proximal portion of an optical fiber 30 to connect a light source 64, such as an LED 64 or laser, to the optical fiber 30. An ECG connector 62 may also be provided along the proximal portion of a conductive wire 40, which in this embodiment is the conductive medium 40, to connect an ECG machine to the wire 40.

Although the optical fiber 30 is shown in the figures as a single, unitary member, it is understood that the optical fiber 30 may have various layers that make up the complete fiber 30. For example, optical fibers 30 typically include a core made of glass or plastic and a cladding layer surrounding the core. In addition, the optical fiber 30 may also be provided with a scratch resistant coating and a slick outer coating to reduce frictional sliding forces during use. The conductive wire 40 may be any type of elongate non-liquid material that conducts an electrical signal along its length. The conductive wire 40 may also be any type of conductive member 40 made of a metallic material and electrically connected to the ECG machine.

Figure 4:
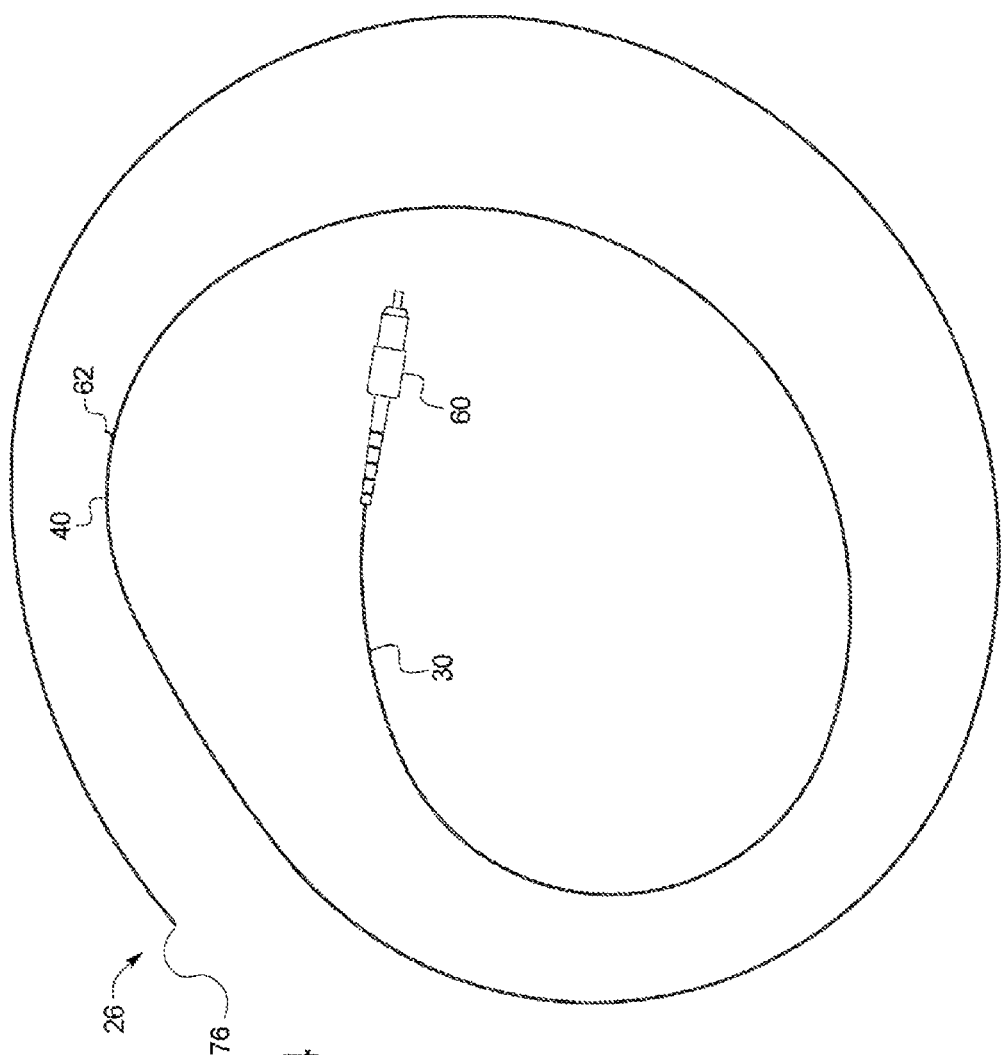
FIG. 4 is an elevational view of the locating device.
Figure 5:
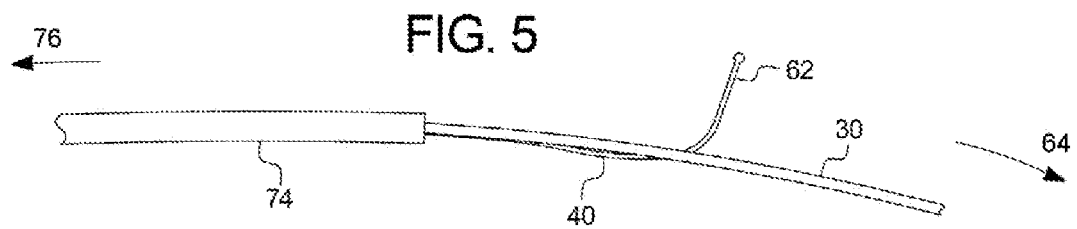
FIG. 5 is a close-up view of an ECG connector on the locating device.

FIG. 4 shows the locating device 26 by itself without the PICC 12, LED 64, and ECG connection cable 66. The light source connector 60 may be a conventional optical fitting for connecting an LED 64 to the optical fiber 30, or may be a special fitting that prevents high powered light sources, which may be harmful, from being connected to the optical fiber 30. As also shown in FIG. 4 (but more visible in FIG. 5), the ECG connector 62 may be merely the proximal end of the conductive wire 40. Thus, in the embodiment shown in FIG. 3, an ECG extension cable 66 with an alligator clip 68 may be connected to the ECG connector 62. The other end of the extension cable 66 may be provided with a conventional ECG electrode snap 70 for connecting an ECG lead 72 to the extension cable 66.

Figure 6:
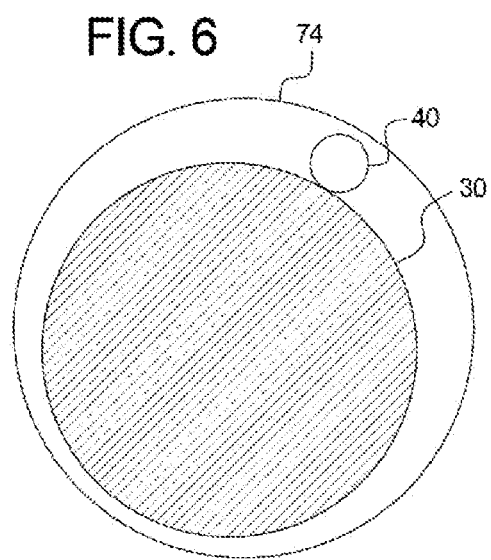
FIG. 6 is a cross-sectional view of one embodiment of the locating device.
Figure 7:
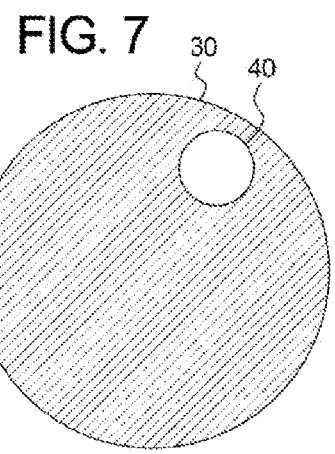
FIG. 7 is a cross-sectional view of another embodiment of the locating device.
Figure 8:
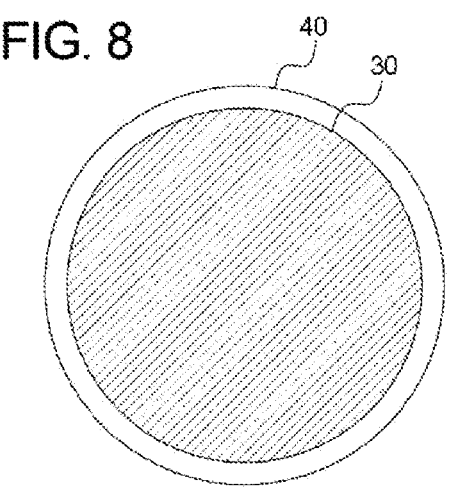
FIG. 8 is a cross-sectional view of another embodiment of the locating device.

Preferably, the optical fiber 30 and the conductive wire 40 are bonded together to longitudinally restrain movement between the optical fiber 30 and the conductive wire 40. This may be done in several ways. For example, in FIG. 6, the optical fiber 30 and the conductive wire 40 may be located side-by-side, and an outer layer 74, such as heat shrink tubing 74, may cover the optical fiber 30 and conductive wire 40 to bond them together. Adhesive or short sections of tubing may also be used. Alternatively, as shown in FIG. 7, the conductive wire 40 may extend longitudinally through the optical fiber 30. In this embodiment, it may be desirable for the conductive wire 40 to be off-center from the axis of the optical fiber 30 to minimize interference with light transmission through the optical fiber 30. As shown in FIG. 8, the optical fiber 30 may also extend longitudinally through the conductive wire 40. In this embodiment, it may be desirable for the conductive wire 40 to be a thin conductive polymer coating 40 on the optical fiber 30. The outer conductive wire layer 40 may also be a thin metal layer or a helical coil wrapped around the optical fiber 30. Thus, the optical fiber 30 would be located coaxially within the conductive wire 40.

A cross-section of the proximal portion of one embodiment of the locating device 26 is shown in FIG. 9A, and the distal portion of the locating device 26 is shown in FIG. 9B. As shown in FIG. 9A, the light source connector 60 may be at the proximal end of the optical fiber 30 and may be coaxial with the optical fiber 30. The ECG connector 62 may be a conventional ECG electrode snap 62 that is fixedly attached to the conductive wire 40. As shown, the conductive wire 40 may extend through a portion of the light source connector 60, and the ECG connector 62 may be located on the light source connector 60. In FIG. 9A-9B, the optical fiber 30 and conductive wire 40 are bonded to each other side-by-side with heat shrink tubing 74 like FIG. 6, but other embodiments could be used as explained above. As shown in FIG. 9B, the redirection element 32 may be a length of the optical fiber 30 with a roughened outer surface 32. As shown, it may be desirable to provide multiple regions 32 with a roughened outer surface 32 to achieve the desired amount of radial light dispersion. Typically, the roughened outer surface 32 will be a length of the optical fiber 30 where the cladding layer has been partially or completely removed to allow light traveling through the core to escape laterally from the core. However, there may be other ways to provide a redirection element 32 along the distal portion of the optical fiber 30, such as altering the crystal structure of the fiber 30 or providing mirrors to redirect the light.

As also shown FIG. 9B, the distal end of the locating device 26 preferably has an atraumatic tip 76. This may be a rounded metal or other conductive tip 76 that is attached to the conductive wire 40. An atraumatic tip 76 is preferable since the distal end of the locating device 26, including the optical fiber 30 and conductive wire 40, are preferably adjacent the distal end of the PICC 12. However, in other embodiments like FIGS. 12-14, where the conductive member does not extend to the distal end of the locating device, the distal end of the optical fiber 30 may be rounded to form an atraumatic tip. As explained above, it may be desirable to lock the locating device 26 and PICC 12 together. Thus, where the locating device 26 and PICC 12 are navigated and positioned through the venous system together, the atraumatic tip 76 of the locating device 26 may extend slightly beyond the distal end of the PICC 12 and form the leading end as the locating device 26 and PICC 12 move through the venous system. Thus, in this embodiment, the distal portion of the conductive wire 40 will be exposed to blood within the patient adjacent the distal end of the PICC 12, as compared to embodiments described below where the conductive wire 40 is only exposed to the biocompatible fluid 80 within the PICC 12. After the locating procedure is complete, the locating device 26 will typically be removed from the lumen of the PICC 12 to allow the PICC 12 to be used in a conventional manner.

The length of the locating device 26 must be sufficient to extend from outside the access site 14 into the patient's venous system to the superior vena cava 18. Thus, when the locating device 26 has been finally positioned in the superior vena cava 18, the proximal portions of the optical fiber 30 and conductive wire 40 and respective connectors 60, 62 will be located outside the patient's body 10. At final positioning, the distal ends of the optical fiber 30 and conductive wire 40 will be located within the superior vena cava 18 or right atrium. The length of the locating device and the location of the connectors 60, 62 outside of the patient's body may be influenced by the desired sterilization field around the access site and which components in the system are sterilized and which are not. For example, it may be possible for the light source 64 to be a reusable device that is sterilizable by a physician. If the light source 64 is sterilized, the light source connector 60 may be located close to the access site 14 in the final position. This may be desirable to keep the optical fiber 30 relatively short and maximize light transmission. Also, if it is desirable to locate the ECG connector 62 close to the access site 14 in the final position, it may be desirable to provide a separate ECG connection cable 66 with the locating device 26, 78, 96, 114 that has been sterilized by the manufacturer. Alternatively, if the light source 64, or proximal member 64, is not sterilized and/or a separate sterilized ECG connection cable is not desirable, one or both of the connectors 60, 62 may be spaced away from the access site 14 during the procedure by an acceptable sterilization field distance. For example, the ECG connector 62 and light source or electric supply line connector 60 may be located at least 150 mm from the access site 14 when the distal portion of the conductive wire 40 and optical fiber 30 are within the superior vena cava 18. Alternatively, it may be more desirable for the ECG connector 62 and light source connector 60 to be at least 1,000 mm from the access site 14 when the distal end of the locating device 26 is within the superior vena cava 18. This may be done by lengthening one or both of the conductive wire 40 and optical fiber 30 to achieve the desired sterilization field.

Figure 11:
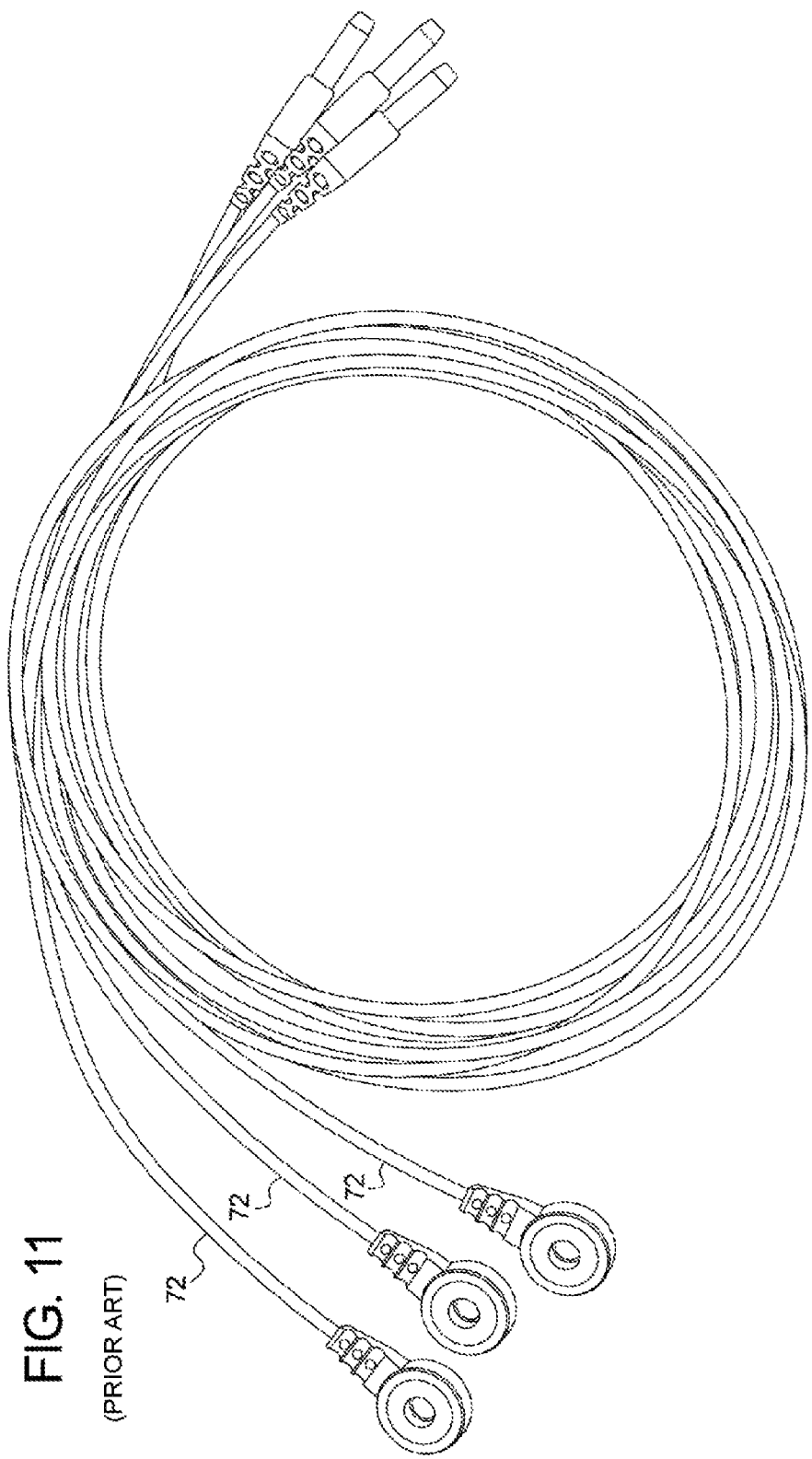
FIG. 11 is an elevational view of conventional ECG leads.

As shown in FIG. 10, the light source or electric supply connector 60 and ECG connector 62 may be separated from each other in order to more easily manage the connectors 60, 62 and use the device 26. Like FIG. 9A (and unlike FIG. 3), it may be preferable for the conductive wire 40 to have a conventional ECG electrode snap 62, such as a button snap 62, fixedly attached to the conductive wire 40. If a conventional ECG electrode snap 62 is provided on the conductive wire 40, a conventional ECG lead 72 like one of the three shown in FIG. 11 may be used to connect the ECG machine to the conductive wire 40. This may be more convenient and intuitive because as explained above conventional ECG leads 72 will also be typically used during the procedure to connect to external electrodes 52 on the patient's torso.

Figure 12:
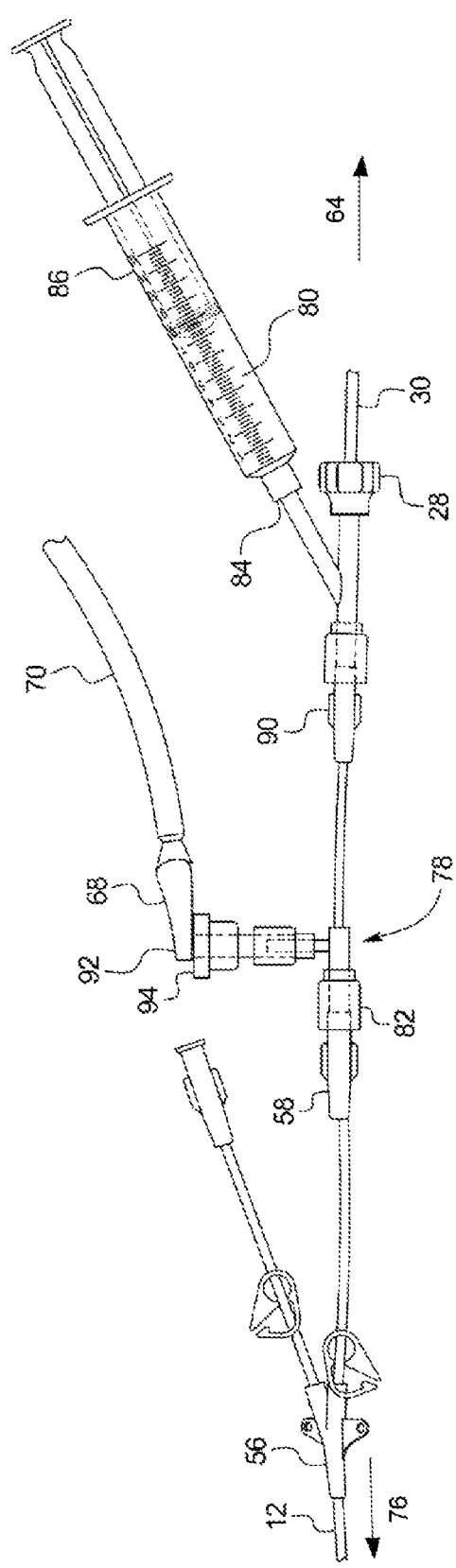
FIG. 12 is an elevational view of another locating device.

An alternative device 78 and method is shown FIG. 12. In this device 78, the conductive medium 80 may be a biocompatible fluid 80, such as saline solution 80, instead of a conductive wire 40. The device 78 may include a hub 82 that can be connected to the second hub 58 of the PICC 12. The device 78 may also include two other ports 84, 90, and a connector hub 94. One port 84 may be connected to a syringe 86 filled with saline solution 80. The optical fiber 30 may extend through another port 90 and through one of the lumens of the PICC 12. Preferably, the port 90 for the optical fiber 30 is generally aligned with the lumen of the PICC 12. A valve 28, such as a tuohy-borst valve 28, may also be connected to the port 90 and may be used to seal and lock the optical fiber 30 in place. A short conductive wire 92 may extend through the connector hub 94 so that the end of the wire 92 inside the device 78 is in contact with the saline solution 80 that fills the device 78. However, in this embodiment, the wire 92 need not extend into the PICC 12. Instead, the saline solution 80 extends through the annular space between the optical fiber 30 and the lumen of the PICC 12 or through a separate lumen of the PICC 12. Because the saline solution 80 is conductive, an ECG reading 42 from the distal end of the PICC 12 can be transmitted to the short conductive wire 92. As shown, an alligator clip 68 can be connected to the short conductive wire 92 to transmit the ECG signal 42 to the ECG machine or an ECG electrode snap 62 can be provided for an ECG lead 72 as explained above. In this embodiment, it may be particularly helpful to press the syringe 86 when the distal end of the PICC 12 enters the superior vena cava 18 to discharge saline 80 from the distal end of PICC 12 to ensure that the lumen of the PICC 12 is completely filled with saline solution 80 to improve transmission of the ECG reading 42. Although already noted above, the conductive wire 92 may be any type of conductive member 92 that is made of a metallic material and is electrically connected to the ECG machine.

Figure 13:
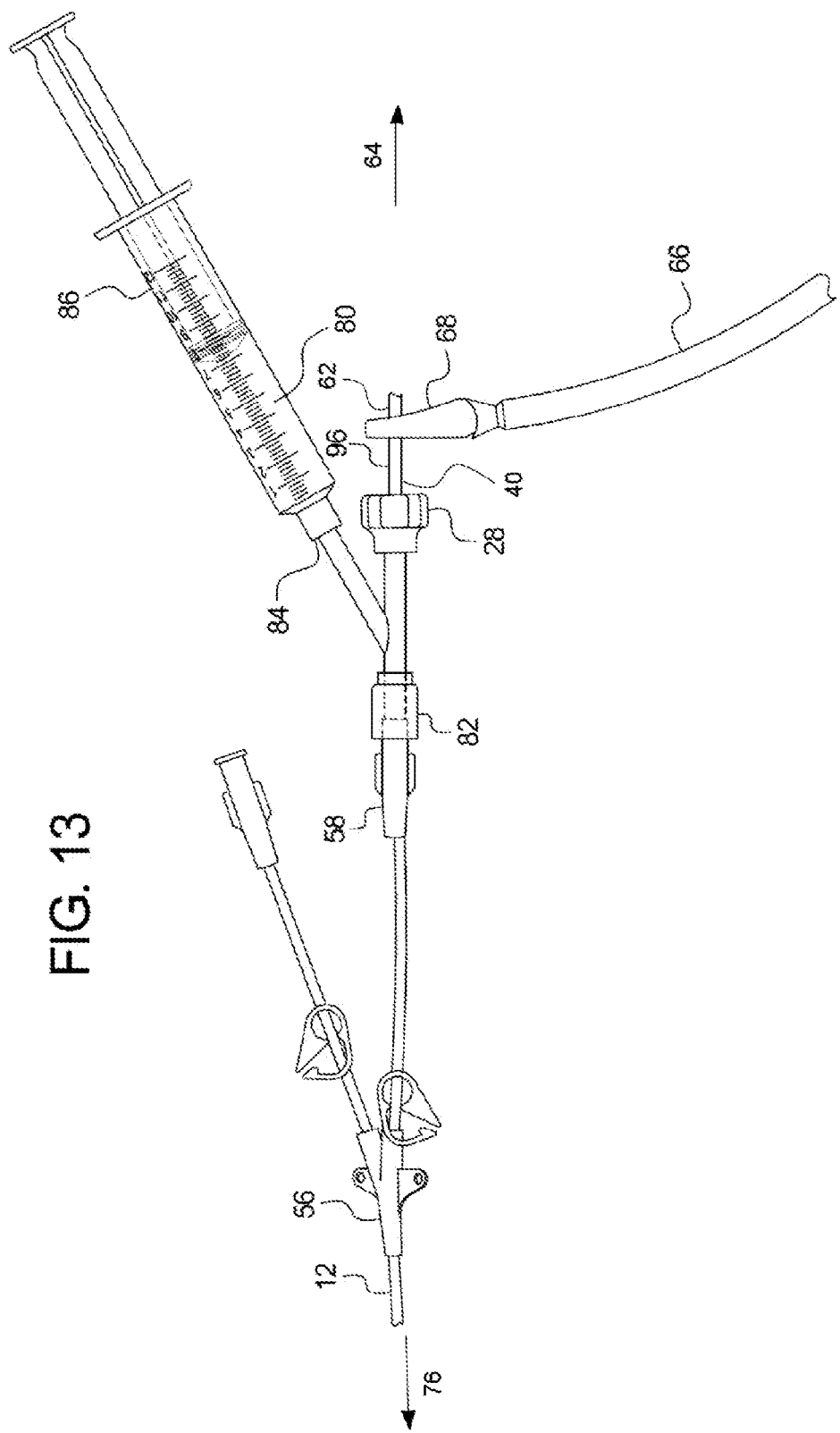
FIG. 13 is an elevational view of another locating device.
Figure 14:
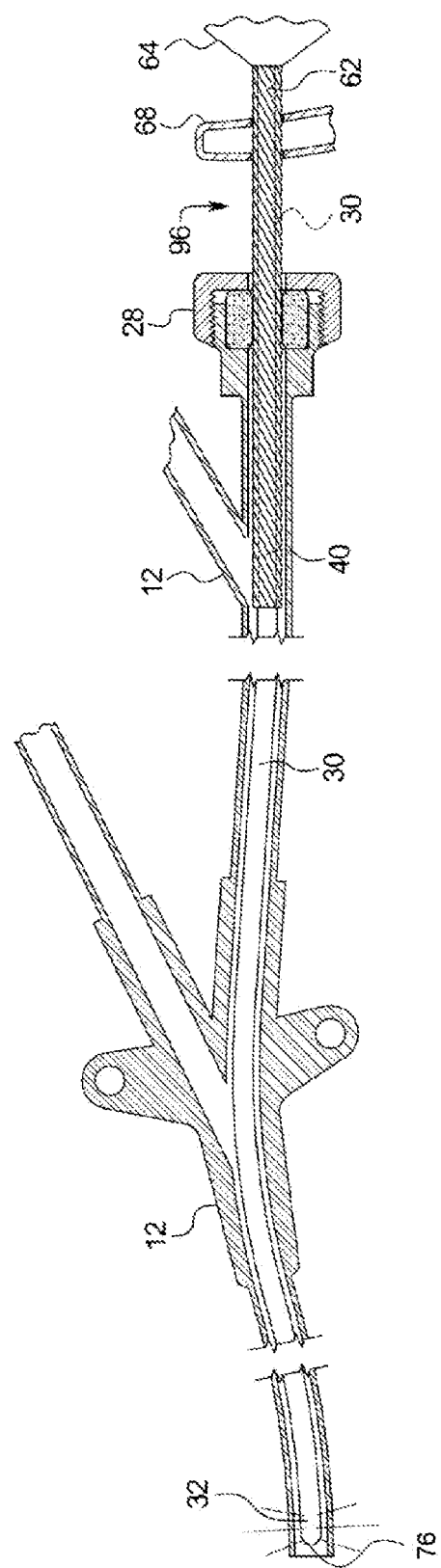
FIG. 14 is a cross-sectional view of the locating device of FIG. 13.

Another embodiment of the locating device 96 and method is shown in FIGS. 13-14. As shown in FIG. 14, the locating device 96 extends through the valve 28 in order to extend through the lumen of the PICC 12. Biocompatible fluid 80, such as saline solution 80, fills the lumens of the PICC 12 and surrounds the locating device 96 but is prevented from escaping by the valve 28. Like the embodiment shown FIG. 8, the conductive wire 40 wraps around the outer circumference of the locating device 96. For example, the conductive wire 40 may be a helical coil 40 that wraps around the optical fiber 30 or around the locating device 114 shown in FIG. 16. One type of helical coil 40 that may be desirable is a helical hollow strand 40, which is composed of multiple wires positioned side-by-side that wraps helically around a core of the locating device 96. The wrapped conductive wire 40 preferably extends distally through the valve 28 so that it is exposed to the biocompatible fluid within the lumen of the PICC 12. The wrapped conductive wire 40 also preferably extends proximally from the valve 28 so that the conductive wire 40 is exposed outside of the access site. This exposed region may be used as an ECG connector 62. Thus, an alligator clip 68 may be used to connect the conductive wire 40 to the ECG machine by clipping the alligator clip 68 onto the outer circumference of the locating device 96. For example, it may be desirable to use an ECG extension cable 66 as shown in FIG. 3 to connect the conductive wire 40 to the an ECG lead 72.

Although the conductive wire 40 in FIGS. 13-14 may extend axially to the distal portion of the locating device 96 like shown and described above (although the wire 40 would not wrap around the light emitting element 32), it may be more desirable for the conductive wire 40 to extend axially through the lumen of the PICC 12 less than half of the overall length of the PICC 12. A shorter conductive wire 40 such as this may provide several advantages. Because the conductive wire 40 does not extend all the way to the distal end of the PICC 12, the method of transmitting the ECG signal 42 is similar to the method shown in FIG. 12, since it relies on the saline solution 80 in the PICC 12 to transmit the ECG reading 42 from the distal end of the PICC 12 to the conductive wire 40. However, this method generally provides similar results to extending the conductive wire 40 all the way to the distal end of the PICC 12. However, because the conductive wire 40 does not extend all the way to the distal end of the locating device 96, the distal portion of the locating device 96 may be more flexible and smaller in profile. This may be particularly advantageous where the PICC 12 tapers to a smaller lumen along the distal portion. Thus, the length of the proximal portion of the locating device 96 with the conductive wire wrap 40 may be sized so that it is only located within the proximal portion of the PICC 12 with the larger lumen, and only the distal portion of the locating device 96 without the conductive wire wrap 40 is located within the smaller lumen that is distal from the taper in the PICC 12.

Typically, it will be preferred for the length of the conductive wire wrap 40 to be at least 30 cm long to allow sufficient length proximally from the valve 28 to connect a clip 68 and to provide sufficient length to accommodate normal trimming of the PICC 12 by physicians. That is, physicians normally trim the end of the PICC 12 to fit a patient's specific anatomy. Thus, when the distal end of the locating device 96 is aligned with the distal end of the PICC 12 after trimming, the proximal portion of the locating device 96 that extends outside of the valve 28 will vary from patient to patient. Thus, the length of the conductive wire wrap 40 is preferably long enough so that at least a portion of the conductive wire wrap 40 will extend distally past the valve 28 and into the lumen of the PICC 12, even where the end of the PICC 12 has been trimmed to fit a patient (in this example, extra fittings connected to the proximal end of the PICC 12 are treated as being part of the PICC 12). Although FIGS. 13-14 contemplate the use of a conductive wire 40 that wraps around the outer circumference of the locating device 96, a minimum and/or maximum length like this would be applicable to any type of conductive wire 40 that is bonded to the locating device 96 to restrain longitudinal movement between the locating device 96 and the conductive wire 40. For example, the conductive wire 40 could have an exposed portion or an electrode snap 62 proximal from the valve 28 and an exposed portion distal from the valve 28. However, the intermediate portion between the exposed portions could be covered and insulated like in FIGS. 6 and 7 if desired.

Figure 15:
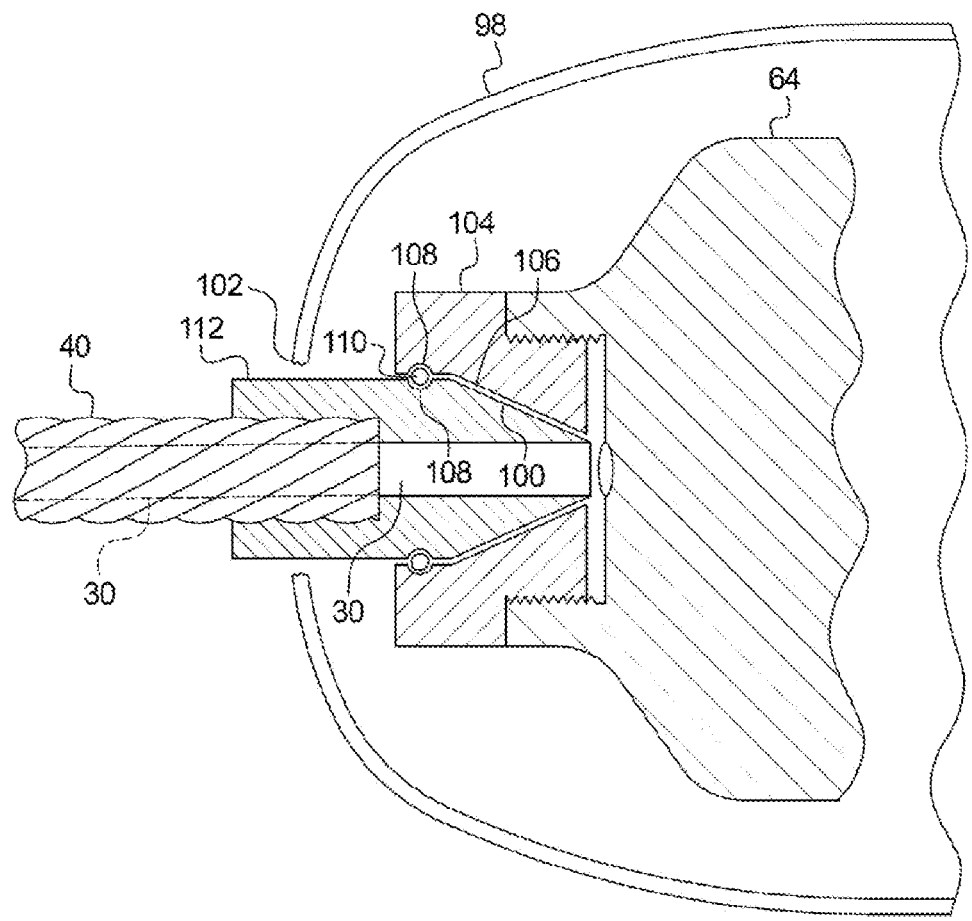
FIG. 15 is a cross-sectional view of a proximal member with an adapter and proximal hub of another locating device within a sterilized bag.

As shown in FIG. 15, a sterilization system may be provided to shorten the length of the locating device 96 that must extend from the proximal end of the PICC 12 to the proximal member 64 housing the light source 64 or power supply 120. This system may be useful where the proximal member 64 is a reusable device that will be used for locating a number of different PICCs 12. For example, the proximal member 64 may be an LED light source 64 or a battery-powered supply unit 120 that is too expensive to be discarded after a single use. However, because the proximal member 64 may be reusable, there may be concerns about sterilization of the proximal member 64, especially where the proximal member 64 cannot withstand standard sterilization procedures. The sterilization system includes a sterile bag 98, or other sterile barrier 98, made from a plastic or other material that can be readily punctured. The proximal member 64 is placed in the sterile bag 98 and sealed inside of the bag 98. The proximal portion of the locating device 96 is provided with a conical surface 100 that narrows to a small proximal end that is suitable for puncturing an opening 102 through the sterile bag 98. After the proximal end of the locating device 96 punctures through the sterile bag 98, the proximal portion of the locating device 96 can be connected to the proximal member 64 inside of the sterile bag 98. Because the sterile bag 98 isolates the proximal member 64 inside of the bag 98, it may be possible to locate the proximal member 64 closer to the access site 14 and the proximal end of the PICC 12 and shorten the overall length of the locating device 96. Also, because the sterile bag 98 is made of a thin, flexible material, a physician can operate the controls of the proximal member 64 during the procedure without directly contacting the proximal member 64.

Although the proximal portion of the locating device 96 and the connection to the proximal member 64 may be configured in a variety of ways, FIG. 15 shows an adapter 104 threaded into the proximal member 64. The adapter 104 allows a conventional proximal member 64 to be used with the sterilization system described above. The adapter 104 is provided with an inverted conical surface 106 that receives the conical surface 100 of the locating device 96. The adapter 104 and the locating device 96 are also provided with one or more recesses 108 to receive a locking ring, ball or other member 110 to allow the locating device 96 and proximal member 64 to be snapped together. In place of the connector 60 of FIG. 3, the proximal portion of the locating device 96 may also be provided with a proximal hub 112 that surrounds the conductive wire wrap 40 and an optical fiber 30 or electrical supply line 118 extending through the wrap 40. Where the distal end of the optical fiber 30 or electric supply line 118 extends distally from the conductive wire wrap 40, the proximal hub 112 may serve to bond the conductive wire wrap 40 and optical fiber 30 or electric supply line 118 together at the proximal end. Alternatively, the proximal hub 112 may also be used without the conductive wire wrap 40 with only the optical fiber 30 like the connector 60 of FIG. 3. As shown, the conical surface 100 and recesses 108 may be formed onto the proximal hub 112. Although FIG. 15 shows the proximal member 64 as being an LED light source 64 and the locating device 96 having an optical fiber 30, it is understood that the proximal member 64 could also be a power supply 120 and the locating device 96 could have an electric supply line 118 connected to the proximal member 64.

Figure 16:
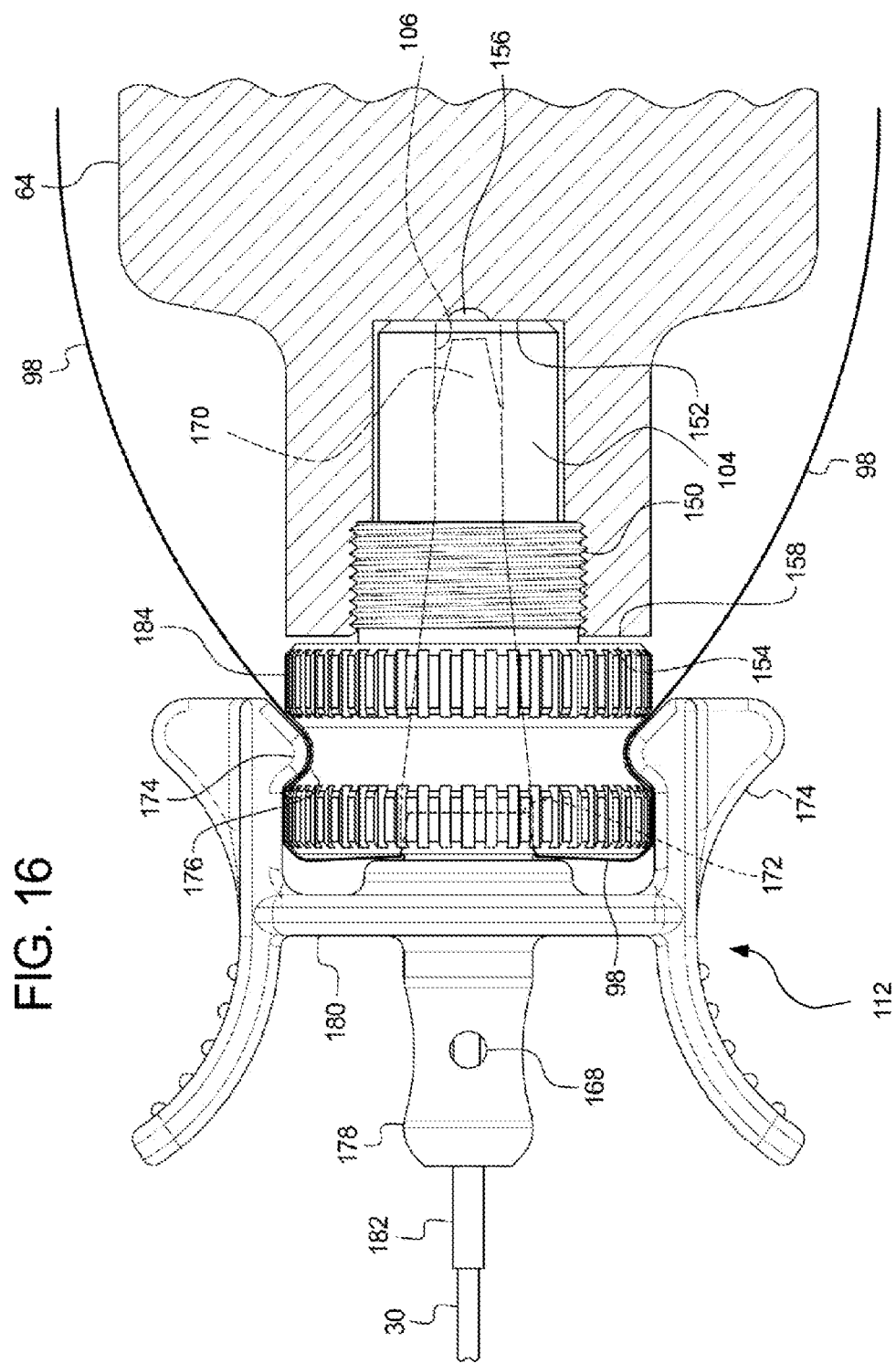
FIG. 16 is a partial cross-sectional view of an alternative embodiment of a proximal member with an adapter and proximal hub of a locating device.
Figure 17:
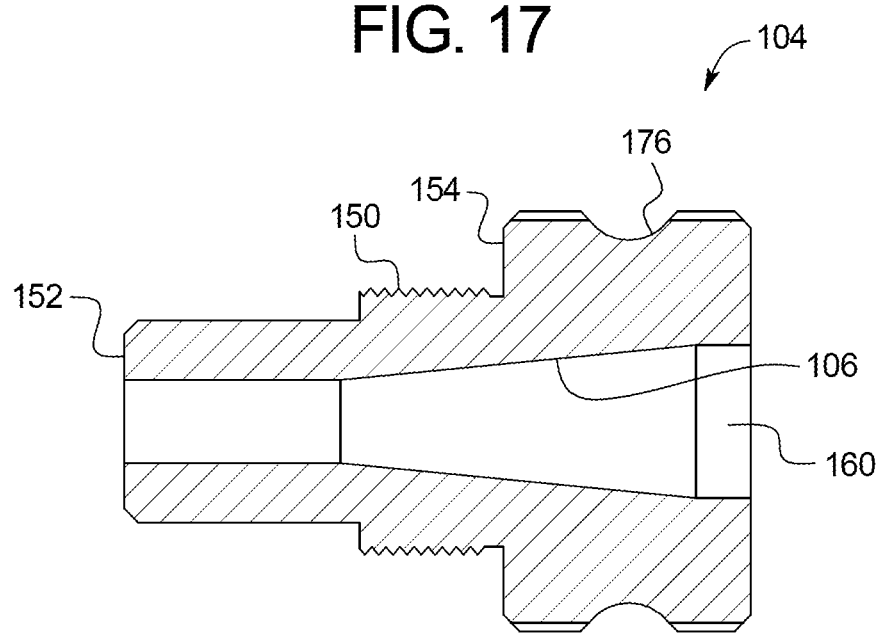
FIG. 17 is a cross-sectional view of the adapter of FIG. 16.
Figure 18:
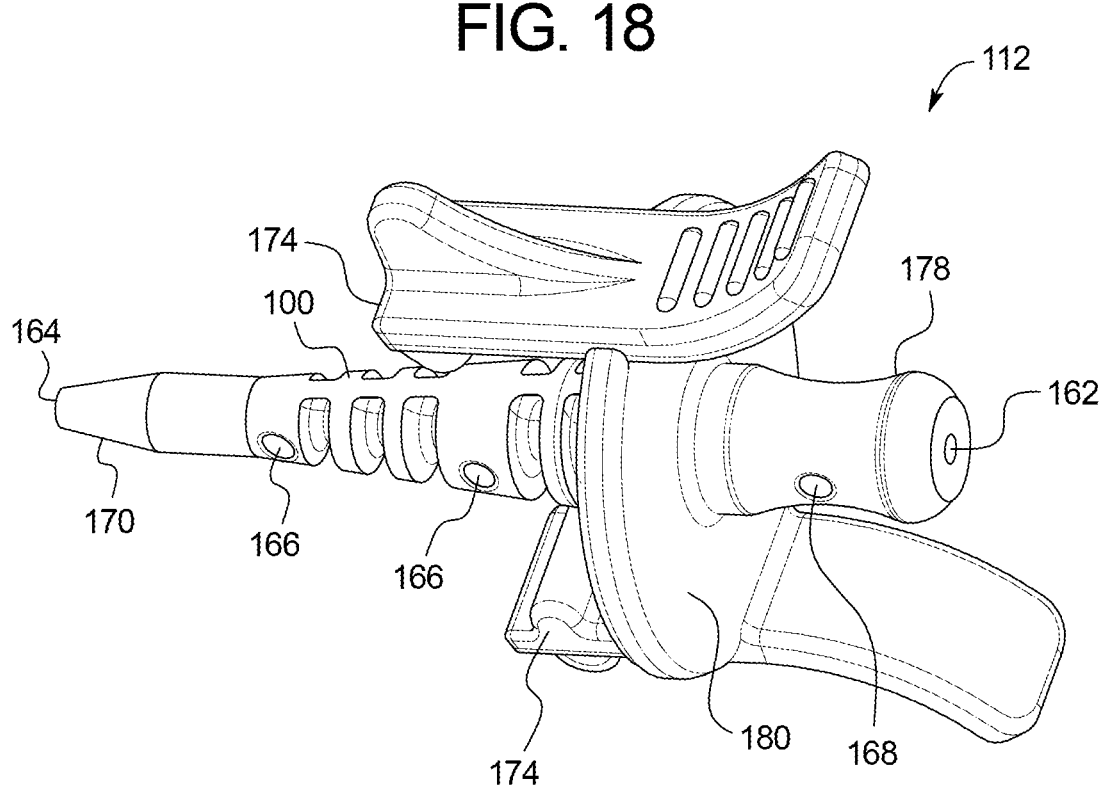
FIG. 18 is a perspective view of the proximal hub of FIG. 16.
Figure 19:
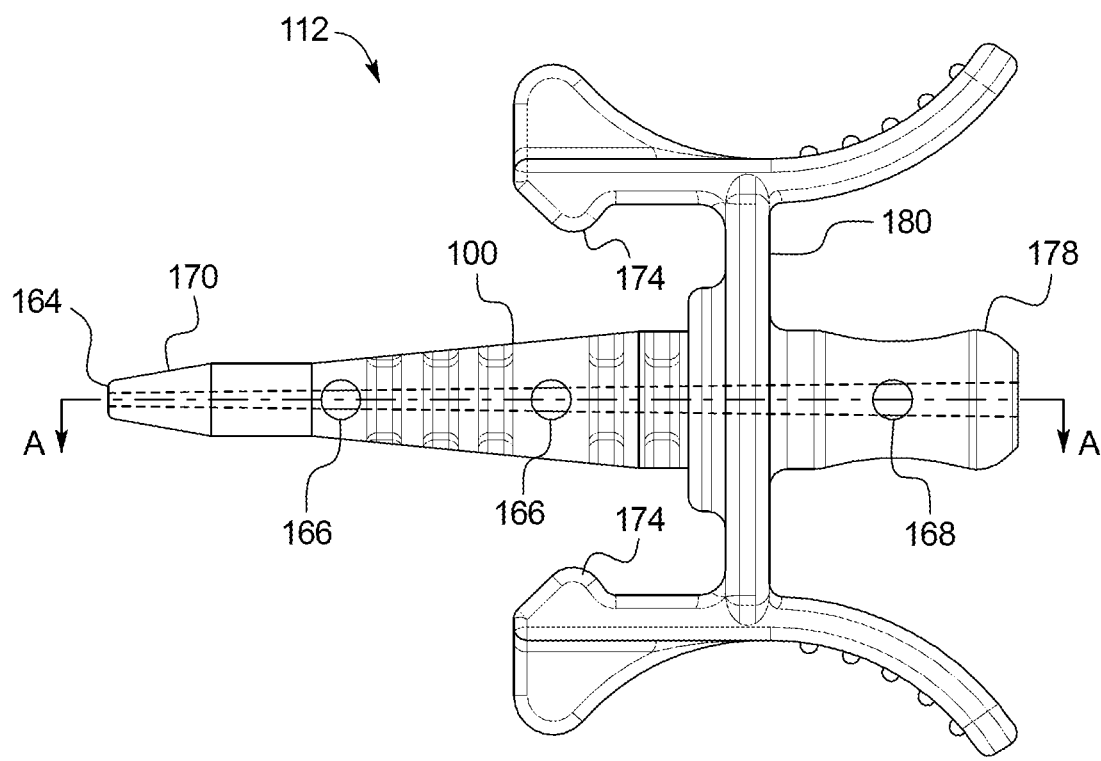
FIG. 19 is a side view of the proximal hub of FIG. 16.
Figure 20:
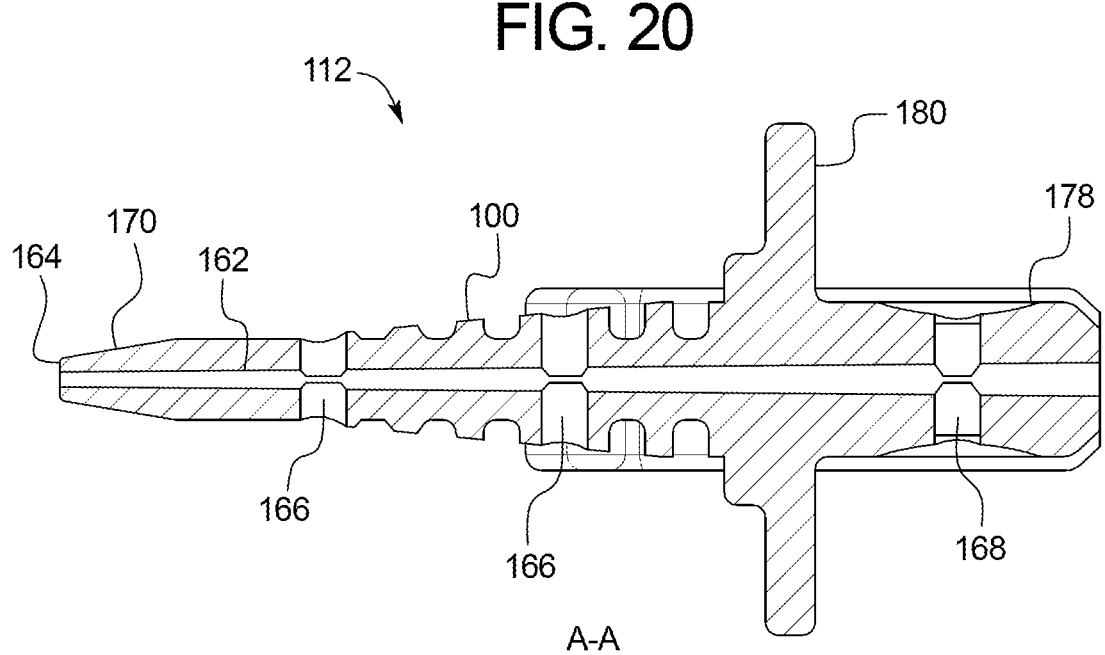
FIG. 20 is a cross-sectional view of the proximal hub of FIG. 16.

As shown in FIGS. 16-20, another variation of the adapter 104 and proximal hub 112 are shown. Although similar to the adapter 104 and proximal hub 112 described above and shown in FIG. 15, the adapter 104 and proximal hub 112 of FIGS. 16-20 include additional features. As shown in FIGS. 16-17, the adapter 104 has threads 150 that are tightened into the threads of the proximal member 64 to connect the adapter 104 and proximal member 64 together. The length between the bottom face 152 of the adapter 104 and the middle flange face 154 may be larger than the length between the LED lens 156 and the end face 158 of the proximal member 64. As a result, when the adapter 104 is fully tightened into the proximal member 64, the bottom face 152 of the adapter 104 preferably bottoms out against the LED lens 156, or inner face 156, of the proximal member 64 before the middle flange face 154 abuts the end face 158 of the proximal member 64. As illustrated in FIG. 17, the inner lumen 160 of the adapter 104 has an inverted conical surface 106 that receives the conical surface 100 of the proximal hub 112. If desired, the inner lumen 160 may also have constant diameter sections corresponding to the proximal hub 112.

The proximal hub 112 has an axial lumen 162 extending therethrough that receives the optical fiber 30. Preferably, the optical fiber 30 extends through the lumen 162 of the proximal hub 112 so that the proximal end of the optical fiber 30 is generally flush with the proximal face 164 of the proximal hub 112. The optical fiber 30 is preferably secured to the proximal hub 112 by gluing the proximal hub 112 and optical fiber 30 together. For example, glue may be deposited into one or more proximal cross holes 166 to directly adhere the proximal hub 112 and optical fiber 30 together. In addition, the optical fiber 30 may be provided with a strain relief 182 (e.g., a short polymeric outer tube) that extends through the distal portion of the lumen 162 in the proximal hub 112. The distal portion of the lumen 162 may have a larger diameter than the proximal portion to accommodate the strain relief 182. The strain relief 182 thus extends out the distal end of the proximal hub 112 and surrounds a proximal portion of the optical fiber 30 to resist kinking of the fiber 30. The strain relief 182, proximal hub 112, and optical fiber 30 may be secured together by depositing glue into one or more distal cross holes 168 and around the distal opening to adhere the proximal hub 112 and strain relief 182 together. The optical fiber 30 and strain relief 182 may also be secured together by depositing glue around the circumference of the optical fiber 30 at the distal end of the strain relief 182.

The proximal hub 112 may be provided with a proximal end 170 that has a steeper taper 170 than the taper of the conical surface 100. This is useful to provide a puncturing tip 170 that is more effective at puncturing the sterile bag 98. In use, it may be preferable for the punctured opening 172 in the sterile bag 98 to get pulled into the lumen 160 of the adapter 104 by the proximal hub 112 so that the punctured opening 172 is squeezed between the adapter 104 and the proximal hub 112. The proximal hub 112 may also be provided with one or more flexible arms 174 that extend from the body of the proximal hub 112 and engage a portion of the adapter 104. The arms 174 preferably engage a tapered portion 176 of the adapter 104 such that when the arms 174 exert pressure against the tapered portion 176 of the adapter 104, the proximal hub 112 is pulled into the lumen 162 of the adapter 104. Pressure by the arms 174 may be exerted by the resiliency of the arms 174 or may also be exerted by the operator's fingers when the operator pushes on the outer surfaces of the arms 174 to push the proximal hub 112 into the adapter 104. As a result, the proximal hub 112 is pulled into the adapter 104 until the proximal face 164 of the proximal hub 112 (and the proximal end of the optical fiber 30) abuts or is flush with the LED lens 156, or inner face 156, of the proximal member 64. One advantage of this feature is that the proximal end of the fiber 30 is positioned as close as possible to the lens 156 so that little or no light is lost between LED-fiber connection.

As shown in FIG. 16, the sterile bag 98 may extend between the flexible arms 174 and the tapered portion 176 of the adapter 104 if desired. As also shown in FIG. 16, the proximal hub 112 may be provided with a distal stem 178 that extends distally from the base 180 of the flexible arms 174. This may be useful to protect the optical fiber 30 from kinking if the operator inadvertently places a finger on the base 180 of the flexible arms 174 when pushing the proximal hub 112 into the adapter 104.

Figure 21:
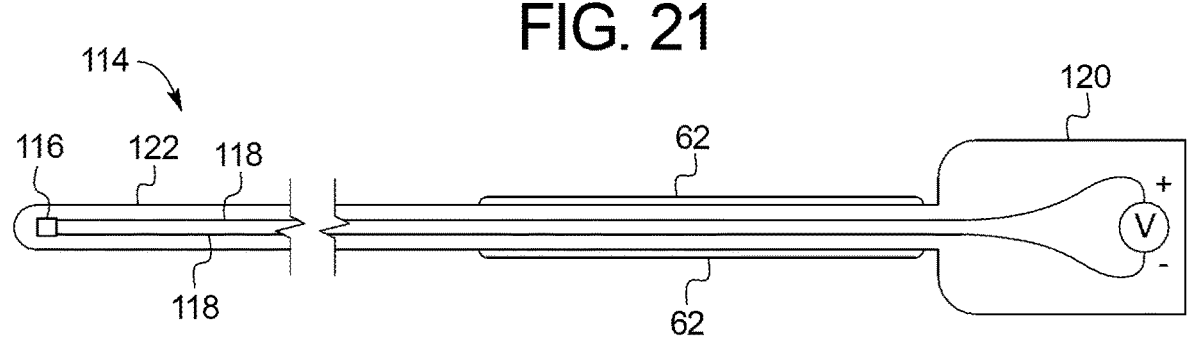
FIG. 21 is a schematic view of another locating device.

As shown in FIG. 21, the locating device 114 may have the light source 116 located along the distal portion of the locating device 114 that extends inside the patient's body instead of at the proximal end as described above. The light emitting element 116 in FIG. 21 is preferably a small LED 116 located near the distal end of the locating device 114. In order to power the LED 116, electric supply lines 118 may extend along the length of the locating device 114 between the LED 116 and the proximal member 120. In this embodiment, the proximal member 120 may have a power supply 120 for the LED 116, which is preferably battery-powered. In order to see the light through the patient's tissues from outside the patient, the LED 116 is oriented laterally from the axis of the locating device 114 so that light is directed radially away from the locating device 114. Preferably, the light source 116 and electric supply lines 118 are embedded within a covering to insulate the electric supply from the patient's body. For example, a resin 122 may be used to cover the LED 116 and electric supply lines 118. Although a single LED 116 is shown, it is understood that the locating device 114 may have multiple LEDs 116 around the circumference and along the length of locating device 114. The LEDs 116 may also be of different colors and may be switched on at different intervals or strobed, etc. if desired.

Figure 22:
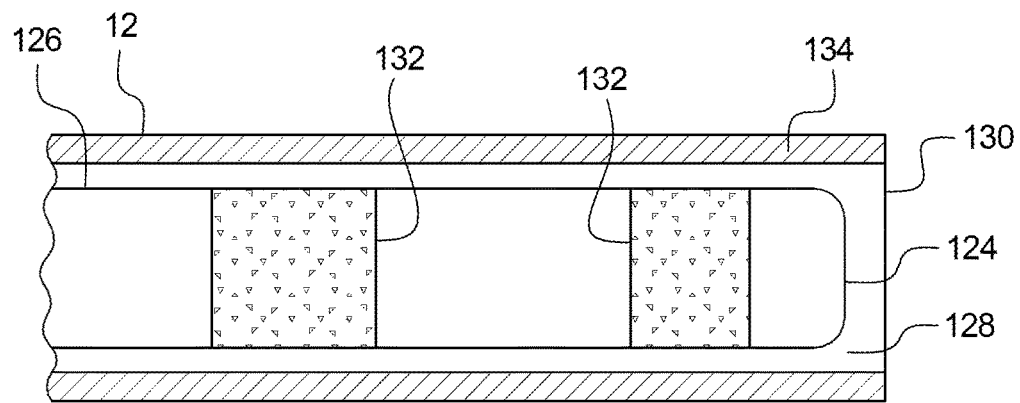
FIG. 22 is a partial cross-sectional view of the distal portion of a iLet another locating device within a catheter.

Another embodiment for a system for navigating a catheter 12 is shown in FIGS. 22-25. As illustrated in FIG. 22, it is preferable in some catheter navigation systems for the distal end 124 of the locating device 126 to be within the lumen 128 of the catheter 12. That is, the distal end 130 of the catheter 12 is located distally from the distal end 124 of the locating device 126 so that the distal end 130 of the catheter 12 forms the leading end 130 of the system. This arrangement is desirable since the distal end 130 of the catheter, for example in the case of a PICC 12, is designed to be atraumatic. It is also preferred for the light emitting element(s) 132 to be located close to the distal end 130 of the catheter 12 in order to indicate to the physician where the distal end 130 of the catheter 12 is during the navigation procedure. Preferably, the distal-most light emitting element 132 is within 50 mm of the distal tip 130 of the catheter 12. Typically, the arrangement of the catheter 12 and the locating device 126 shown in FIG. 22 will be locked together with a proximal valve 28 as shown in FIG. 14 to maintain the relative positions of the catheter 12 and the locating device 126. As explained above, after the catheter 12 is positioned at the intended treatment site, the locating device 126 will be unlocked by releasing the valve 28, and the locating device 126 will be removed from the lumen 128 of the catheter 12.

Figure 23:
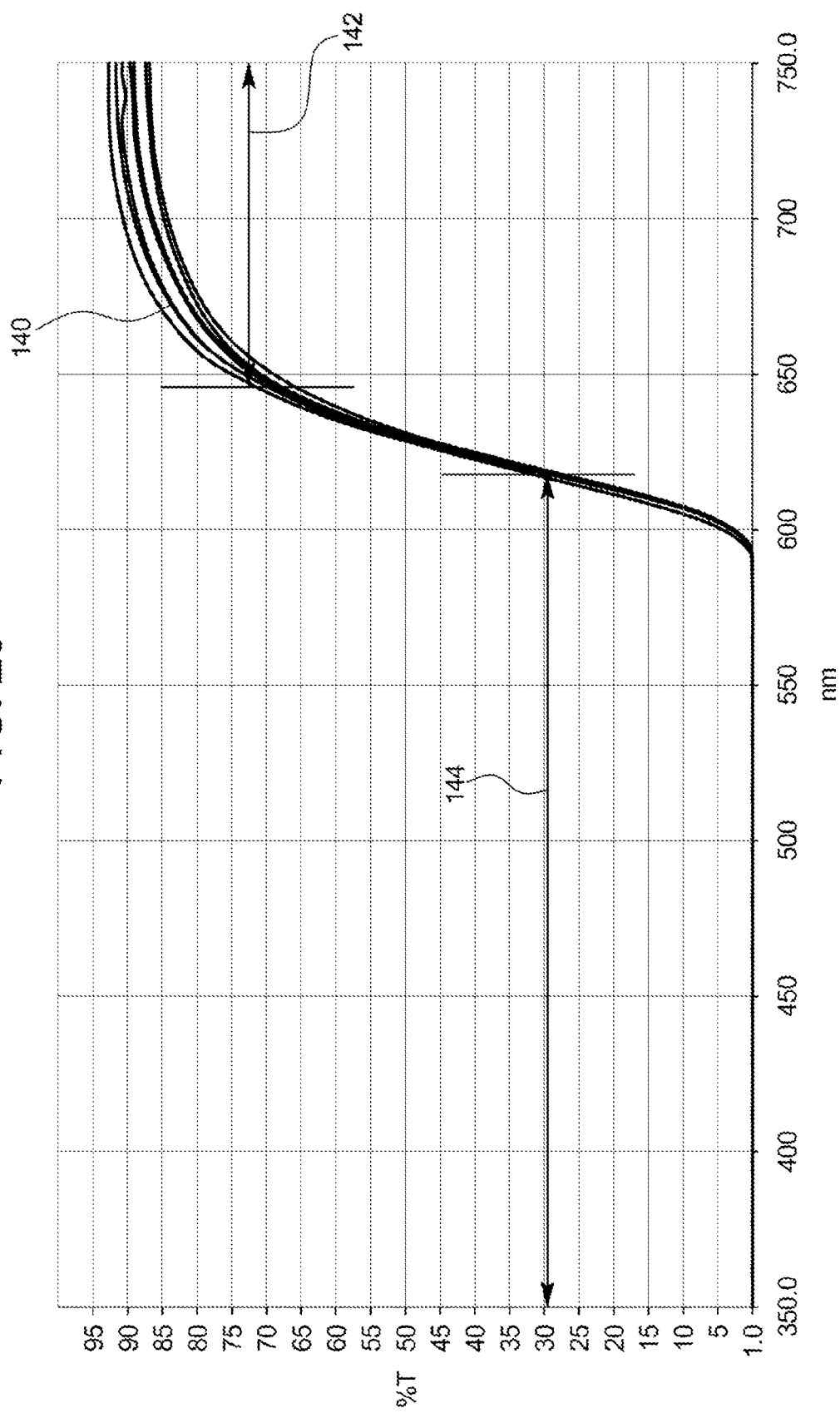
FIG. 23 is a chart showing transmission of light through an additive.
Figure 24:
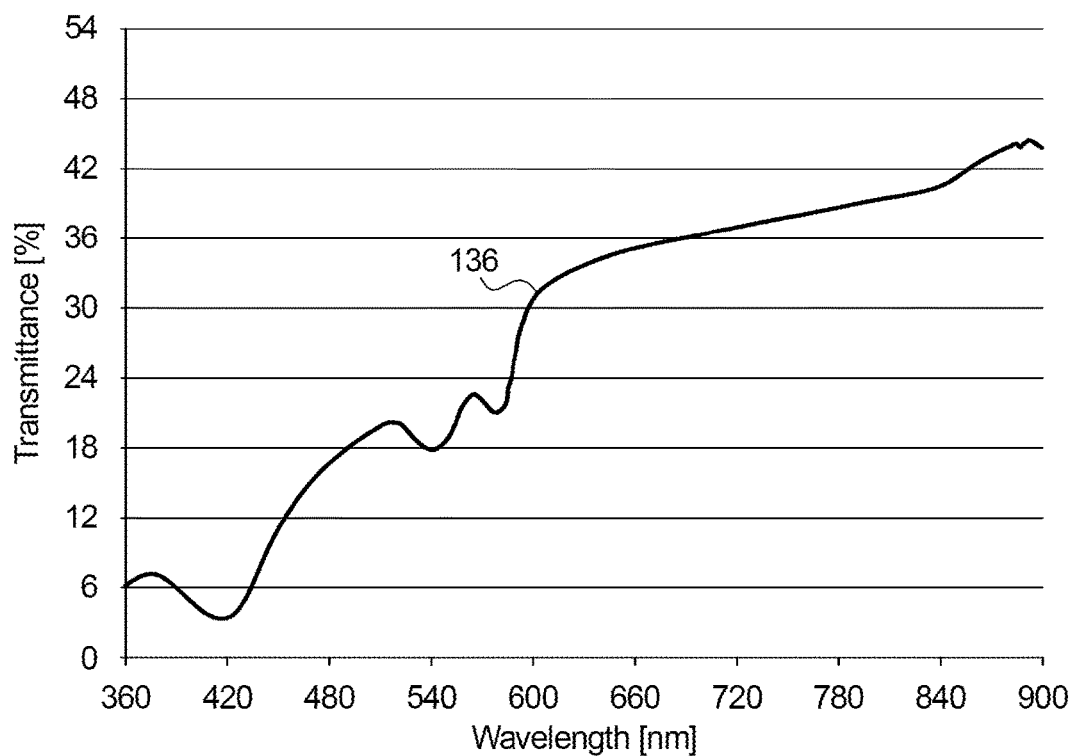
FIG. 24 is a chart showing transmission of light through body tissues.
Figure 25:
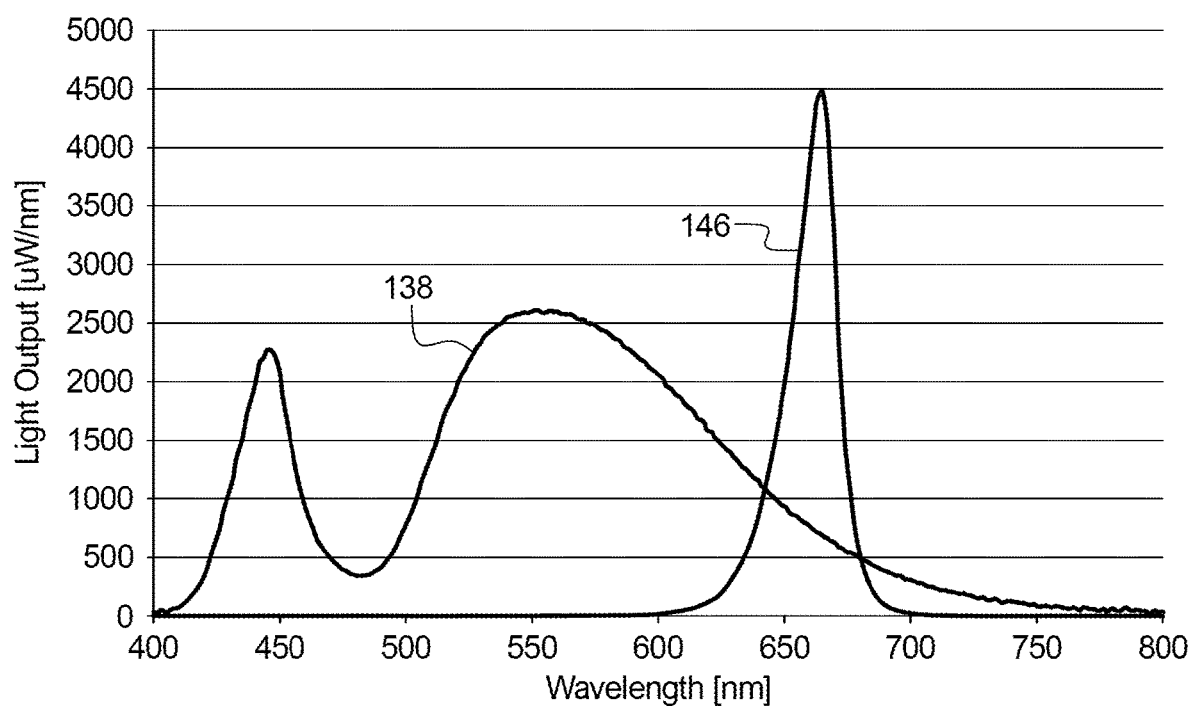
FIG. 25 is a chart showing the wavelengths of light output of a white light source and a red light source.

One problem with navigating the catheter 12 with a light emitting element 132 as arranged in FIG. 22 is that the light from the light emitting element 132 must pass through the tubular wall 134 of the catheter 12 and the overlying tissues of the patient in order for the physician to view the light from outside of the patient. In FIG. 24, a chart is shown which illustrates the typical transmission 136 of various wavelengths of light through body tissues. Although the wavelengths of light illustrated in FIGS. 23-25 may not precisely match the visible light spectrum, the wavelengths of light referred to herein concern the visible light spectrum, since the intention is that the physician will be able to view the light transmitted by the light emitting element 132 from outside of the patient without the aid of special viewing equipment. As illustrated in FIG. 24, all wavelengths of visible light can be transmitted 136 through body tissues to varying degrees. Thus, if the light transmitted by the light emitting element 132 is intended to only pass through body tissues, the wavelengths of light used may not be of particular concern. Thus, one conventional choice that may be used for the light source (e.g., LED 64 in FIG. 3 or LED 116 in FIG. 21) may be a white LED 138. As illustrated in FIG. 25, a white LED 138 emits wavelengths of light over the entire, or most of, the visible light spectrum. Depending on the specific light source used, a white light source 138 may have multiple peaks of higher light output at certain wavelengths, but in general a white light source 138 emits light across a broad range of the visible light spectrum. While some of the white light 138 wavelengths may be diminished more than other wavelengths, in general it would be expected that all white light 138 wavelengths will pass through body tissues to some degree.

However, depending on the type of catheter 12 used, it is possible that the catheter 12 may have a different light transmission profile than overlying body tissues. This may be particularly the case when a additive 140 is added to the tubular wall 134 of the catheter 12 that absorbs certain wavelengths of visible light more than other wavelengths of visible light. One such example of a additive 140 is illustrated in the chart of FIG. 23. Although additives with different transmission profiles may be used, the additive 140 of FIG. 23 may be characterized by a first range 142 of visible light wavelengths and a second range 144 of visible light wavelengths, where the first range 142 of wavelengths allows a higher percentage of light to pass through the additive 140 than the second range 144 of wavelengths allows. Thus, within the second range 144, a higher proportion of light is absorbed by the additive 140 than in the first range 142. That is, light more easily passes through the additive 140 within the first range 142 of wavelengths, but light is either partially or substantially blocked within the second range 144 of wavelengths compared to the first range 142. Thus, as shown in FIG. 23, light transmission is completely blocked within the majority of the second range 144. In FIG. 23, light transmission may also be considered completely blocked within the entire second range 144 where the second range 144 is defined at about 580 nm at the upper end, since this range also constitutes more than 50% of the entire visible light spectrum.

The additive 140 may be a variety of different materials and may be incorporated with the tubular wall 134 of the catheter 12 in a variety of ways. For example, the additive 140 may be impregnated into the tubular wall 134 and may be integrated throughout the tubular wall 134. If desired, the impregnated additive 140 may be exposed to the exterior surface and interior surface of the tubular wall 134. However, the additive 140 may also be a coating applied to the exterior or interior surfaces of the wall 134. Typically, the tubular wall 134 of the catheter 12 will be made of a structural base material, such as a flexible polymer material like nylon, which may define the light transmission profile of the wall 134 in part or in whole. In one embodiment, the additive 140 is a drug 140. For example, the additive 140 may be an antibiotic drug 140. This may be particularly advantageous where the catheter 12 is a central venous catheter 12, such as a PICC 12, since a PICC 12 may be left within a patient's venous system for days or years. Thus, an antibiotic drug 140 incorporated into the tubular wall 134 of the catheter 12 can prevent bacterial growth on the surfaces of the catheter 12. One possible antibiotic drug 140 that may be used is a combination 140 of minocycline and rifampin. Minocycline is typically yellow in color, and rifampin is typically red in color. The resulting combination 140 of minocycline and rifampin is typically orange in color. Preferably, the additive 140 is incorporated along substantially the entire length of the catheter 12. However, for the purposes described herein, the additive 140 is incorporated along at least the distal portion of the catheter 12 where the light emitting element 132 is located. The light emitting element 132 is directed toward the wall 134 of the catheter 12 incorporating the additive 140. Thus, the light from the light emitting element 132 must pass through the additive 140 in order to be seen from outside the patient.

The chart in FIG. 23 shows the percent transmittance 140 of light at various wavelengths through the minocycline/rifampin antibiotic drug combination 140. As shown, the minocycline/rifampin drug combination 140 substantially blocks transmission of the majority of visible wavelengths of light within the second range 144 of wavelengths. However, within the first range 142 of wavelengths, a relatively high proportion of light passes through the drug combination 140. For example, the transmittance of light through the minocycline/rifampin drug combination 140 is higher in the first range 142 of wavelengths than the transmittance of a comparable range of wavelengths through body tissues (compare FIGS. 23 and 24). Preferably, the first range 142 of wavelengths defining the additive 140 is less than 50% of the entire visible light spectrum. Within the first range 142 of wavelengths, at least 70% of light is transmissable through the additive 140. The second range 144 of wavelengths is more than 50% of the entire visible light spectrum. Within the second range 144 of wavelengths, preferably no more than 30% of light is transmissable through the additive 140. In the case of the minocycline/rifampin drug combination 140 described above, the first range 142 of visible light wavelengths may be between 580 nm and 750 nm. Thus, the additive 140 may be orange or red in color.

It is understood that the light transmission profile of the tubular wall 134 is defined by the entire structure and materials that make up the tubular wall 134. Thus, where the tubular wall 134 is made from a structural base material like nylon and an additive 140 impregnated therein like a drug, the light transmission profile of the wall 134 is a combination of the transmission properties of the base material and the additive 140. Conventionally, the base material will typically be made from a material that has generally uniform light transmission throughout the entire visible light spectrum. Thus, conventional base materials commonly have a generally white or other neutral appearance or a shade or hue thereof. By contrast, the additive 140 may have greater light absorbing properties throughout the second range 144 and allows light transmission throughout the first range 142. Thus, the additive 140 may behave like a dye or other pigment. Although the transmission ratio of the additive 140 itself may be quite high within the first range 142 as illustrated in FIG. 23, it is understood that light transmission through the wall 134 may be significantly less where the base material itself blocks a percentage of light throughout the visible light spectrum, or least blocks a percentage of light within the first range 142.

The tubular wall 134 may be characterized as translucent in that at least some light is able to pass through the wall 134 and can be seen with the naked eye. However, when a white light is used, the wavelengths that transmit through the tubular wall 134 can be defined as having a color of red, orange, yellow, green, blue, violet or a mixture thereof. That is, the tubular wall 134 is not white, black or variations thereof. Thus, as explained above with respect to the preferred additive 140, the tubular wall 134 may likewise be defined by a first range 142 of wavelengths that is less than 50% of the visible light spectrum, and a second range 144 of wavelengths that is more than 50% of the visible light spectrum. The color of the tubular wall 134 may therefore be defined by a greater percentage of the first range 142 being transmitted through the wall 134 compared to the second range 144, and a greater percentage of the second range 144 being blocked or absorbed compared to the first range 142. The second range 144 may also be defined as having at least a 15% or a 50% drop in transmission intensity compared to the first range 142. Preferably, no more than 30% of light is transmissable through the tubular wall 134 within the second range 144. Alternatively, the second range 144 may be defined as wavelengths where light transmission is substantially blocked. If desired, the second range 144 may be defined as being at least 75% of the visible light spectrum. More specifically, substantially all of the visible light may be blocked within 75% of the visible light spectrum. Thus, when white light is transmitted through the tubular wall 134, the light transmitted therethrough may be a distinct color of either red, orange, yellow, green, blue or violet, which is understood to include shades thereof.

In order to ensure that sufficient light passes through the tubular wall 134 of the catheter 12 and the overlying body tissues for the physician to be able to see the light from outside the patient, the light output from the light source may be narrowed to a range of wavelengths that generally matches the wavelengths of the first range 142 of wavelengths defining the tubular wall 134. For example, the light output of one embodiment of a preferred light source is shown in FIG. 25. Unlike the light output for white light 138, the light output for the preferred light source 146 emits substantially more visible light within the first range 142 of wavelengths than within the second range 144 of wavelengths. It is also possible for substantially all of the light output of the preferred light 146 to be within the first range 142. Alternatively, there may be substantially no light output within the second range 144. Preferably, at least 60% of the light output of the light source 146 is within the first range 142 of wavelengths, and no more than 30% of the light output 146 is within the second range 144 of wavelengths. Typically, light output may be measured as a power density within a particular range of wavelengths. An LED may be preferred for the light source 146, since an LED may provide light with a single peak of wavelengths of light as shown in FIG. 25. By way of comparison, in FIG. 25 where a similar white LED 138 and red LED 146 were used, the power density of the red LED 146 within the range of 600 nm and 700 nm is more than nine times higher than the white LED 138 within the 600-700 nm range. A power density for the light source of more than five times a comparable white light source 138 within the first range 142 may also be advantageous. Preferably, at least 60% of the light output of the light source 146 is within 600 nm and 700 nm. Thus, the light output may be orange or red and the tubular wall 134 may be orange or red, and preferably orange, when used together in the light navigation method described above.

Because the wavelengths of light emitted from the light source 146 generally matches the first range 142 of wavelengths of light that are transmissable through the tubular wall 134, a higher amount of light passes through the wall 134 of the catheter 12. As a result, more light reaches the exterior of the patient to make viewing the light easier for the physician. Alternatively, it would be possible to use a light source 146 with less power and still achieve acceptable exterior visualization for navigation when the wavelengths of light emitted from the light source 146 generally matches the first range 142 of wavelengths of the catheter 12.

While preferred embodiments of the invention have been described, it should be understood that the invention is not so limited, and modifications may be made without departing from the invention. For example, the method and device may be used to navigate and position a central venous catheter into the venous system with the two described modes of location. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

The invention claimed is:

1. A method of locating a central venous catheter within a venous system of a patient, wherein the venous system includes a superior vena cava, the method comprising the following steps:

extending a locating device and a conductive medium from an access site through one or more lumens of the central venous catheter while emitting light from a location adjacent a distal end thereof bright enough to shine through body tissue from the venous system to the patient's skin, to make the location visible to a naked human eye from outside of the patient, and to navigate the locating device through the venous system by viewing the light through the body tissue by a human eye;

establishing access to a vein within an arm or neck of the patient; directing light radially away from the distal end of the locating device;

navigating the central venous catheter through the venous system of the patient until the distal end reaches a location within 15 cm of the superior vena cava by viewing the light from outside of the patient through the body tissue, wherein the central venous catheter comprises a distal portion with a tubular wall defining a lumen extending therethrough, the tubular wall being at least partially translucent and defined by a first range of visible light wavelengths and a second range of visible light wavelengths the first range of visible light wavelengths comprising less than 50% of the entire visible light spectrum and the second range of visible light wavelengths comprising more than 50% of the entire visible light spectrum, the first range being at least partially transmitted through the tubular wall, and the tubular wall blocks transmission of all visible light wavelengths within the second range, wherein the first range appears as a color of red, orange, yellow, green, blue, violet or a mixture thereof when a white light is transmitted through the tubular wall; wherein the locating device extends through the lumen of the catheter with an optical fiber having a distal end disposed along a distal portion thereof, the optical fiber being disposed within the lumen and directing the light toward the tubular wall; wherein a light source is in communication with the optical fiber, at least 60% of light output by the light source being within the first range of visible light wavelengths and no more than 30% of the light output being within the second range of visible light wavelengths, wherein the light output is directed through the tubular wall, the light output being visible from an exterior of the patient through the tubular wall and overlying tissues of the patient for navigation through the venous system; and positioning the distal portion of the central venous catheter within the superior vena cava by monitoring an Electrocardiography (ECG) reading through the conductive medium.

2. The method according to claim 1, wherein the locating device comprises an optical fiber extending from the proximal portion of the locating device to the distal portion of the locating device, a redirection element disposed along the optical fiber, the redirection element directing light passing axially through the optical fiber radially away from the optical fiber while navigating the locating device toward the superior vena cava, and a light source connected to a proximal end of the optical fiber.

3. The method according to claim 2, wherein the redirection element comprises a partially or completely removed length of a cladding layer of the optical fiber.

4. The method according to claim 2, wherein a distal end of the optical fiber is adjacent the distal end of the central venous catheter.

5. The method according to claim 2, further comprising an adapter connected to the light source and a proximal hub connected to the optical fiber, the proximal hub and the adapter being adapted to couple the light source and the optical fiber together for the transmission of light from the light source to the optical fiber, the proximal hub comprising a flexible arm engaging a tapered portion of the adapter, wherein pressure from the flexible arm against the tapered portion pulls the proximal hub into the adapter until a proximal end of the optical fiber is flush with a lens of the light source.

6. The method according to claim 1, wherein the locating device comprises an electric supply line adapted to extend from the proximal portion of the locating device to the distal portion of the locating device, a light source connected to a distal end of the electric supply line and adapted to direct light radially away from the locating device, and a power supply connected to a proximal end of the electric supply line.

7. The method according to claim 6, wherein the conductive member comprises a coiled wire wrapped around an outer circumference of a length of the locating device.

8. The method according to claim 1, wherein the conductive member wraps around an outer circumference of a length of the proximal portion of the locating device, the conductive member thereby being exposed proximally from the proximal portion of the central venous catheter, and the conductive member being connectable to an ECG machine with a clip contacting the outer circumference.

9. The method according to claim 1, wherein the conductive member extends axially through one of the lumens of the central venous catheter less than half of an overall length of the central venous catheter.

10. The method according to claim 1, wherein the conductive member extends axially through one of the lumens of the central venous catheter along an entire length of the central venous catheter.

11. The method according to claim 1, wherein the locating device extends through a valve to extend through the lumen of the central venous catheter, the valve longitudinally retaining the central venous catheter and the locating device together during navigation and positioning of the central venous catheter.

12. The method according to claim 1, further comprising a proximal member housing a light source or a power supply, a sterile barrier surrounding the proximal member, and a proximal end of the locating device comprises a conical surface configured to penetrate the sterile barrier to connect the locating device to the proximal member.

13. The method according to claim 1, further comprising an ECG extension cable comprising a clip at one end adapted to connect to the conductive member and an ECG electrode snap at another end adapted to connect to an ECG lead.

14. The method according to claim 1, further comprising an ECG electrode snap fixedly attached to the conductive member along a proximal portion of the conductive member.

15. The method according to claim 13, wherein the ECG electrode snap is disposed more than 300 mm from the access site when the distal portion of the conductive member is within the venous system.

16. The method according to claim 1, further comprising a proximal member housing a light source or a power supply connected to a proximal end of the locating device, the proximal member being disposed more than 150 mm from the access site when the distal portion of the locating device is within the venous system.

17. The method according to claim 1, wherein the locating device and the conductive member are bonded together to restrain longitudinal movement between the locating device and the conductive member.

18. The method according to claim 1, wherein the locating device is disposed coaxially within the conductive member.

\* \* \* \* \*